United States Patent
Yanaka et al.

(10) Patent No.: US 6,242,445 B1
(45) Date of Patent: Jun. 5, 2001

(54) BENZIMIDAZOLE DERIVATIVE

(75) Inventors: Mikiro Yanaka, Chiba; Shigeru Suzuki, Kanagawa; Fuyuhiko Nishijima, Tokyo; Hiroshi Takahashi, Fukushima; Mikio Sugano, Tokyo; Hiroshi Maruoka, Tokyo; Toru Yamazaki, Tokyo; Toshikazu Dewa, Tokyo; Hiroyuki Enari, Tokyo; Michihito Ise, Saitama, all of (JP)

(73) Assignee: Kureha Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/622,788

(22) PCT Filed: Feb. 23, 1999

(86) PCT No.: PCT/JP99/00794

§ 371 Date: Aug. 23, 2000

§ 102(e) Date: Aug. 23, 2000

(87) PCT Pub. No.: WO99/42451

PCT Pub. Date: Aug. 26, 1999

(30) Foreign Application Priority Data

Feb. 23, 1998 (JP) .................................................. 10-057497

(51) Int. Cl.[7] ................. A61K 31/5377; A61K 31/4184; C07D 235/26; C07D 235/30
(52) U.S. Cl. ...................... 514/234.5; 514/387; 514/388; 544/139; 548/306.4; 548/307.4
(58) Field of Search ............................ 548/306.4, 307.4; 544/139; 514/387, 388, 234.5

(56) References Cited

FOREIGN PATENT DOCUMENTS 4-364171    12/1992  (JP) .

OTHER PUBLICATIONS

International Search Report for PCT/JP99/00794, Jun. 1, 1999.

*Primary Examiner*—Laura L. Stockton
(74) *Attorney, Agent, or Firm*—Sughrue, Mion, Zinn, Macpeak & Seas, PLLC

(57) ABSTRACT

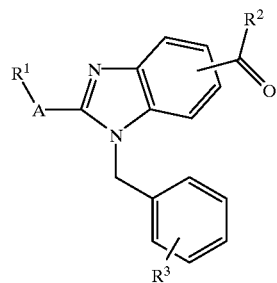

(I)

A novel benzimidazole derivative [specifically, for example, 2-ethoxy-1-[{4'-(2"-N,N-dimethylaminoethoxycarbonyl)phenyl}methyl]-1H-benzimidazole-6-carboxylic acid morpholide] represented by formula (I) and a salt thereof. The compound exhibits satisfactory curative effects for cardiac and nephric diseases, although having little action on blood-pressure.

10 Claims, No Drawings

BENZIMIDAZOLE DERIVATIVE

This application is a 371 of PCT/JP99/00794 filed Feb. 23, 1999.

TECHNICAL FIELD

The present invention relates to a novel benzimidazole derivative or a salt thereof, a pharmaceutical composition, in particular, an agent for treating or preventing kidney disease or heart diseases, containing the benzimidazole derivative or the salt thereof, a treatment method, and the use thereof. The benzimidazole derivative of the present invention exhibits a function sufficient to treat or prevent, in particular ameliorate, kidney or heart diseases, although it exhibits substantially no or a very weak competitive action to an angiotensin II receptor subtype 1 that takes part in a function to lower blood pressure.

BACKGROUND ART

There is now an increasing number of patients suffering from renal dysfunction or heart diseases. This is believed to be because a development of drugs appropriate to the treatment of kidney diseases or heart diseases has lagged behind an increase in the number of senior citizens in the population or changes in the environment. Therefore, drugs appropriate to the treatment of kidney diseases or heart diseases are urgently required.

More particularly, a method for treating lesions accompanying diseases, i.e., a nosotropic treatment, is mainly used for kidney diseases such as nephritis, diabetic nephropathy or renal failure. For example, an antihypertensive agent, diuretic or anti-inflammatory agent, or a dietary treatment, kinesitherapy or the like is used. Because kidney diseases are accompanied by hypertension, and because hypertension is believed to be one of the factors that aggravate kidney diseases, antihypertensive agents are often used. Of the antihypertensive agents, in many cases those that inhibit the production or function of angiotensin II are used. This is because angiotensin II is believed to be a factor aggravating kidney diseases, as it raises the blood pressure and accelerates the growth of interstitial cells in the kidney, and an elimination of such a factor, insofar as possible, is believed to alleviate kidney diseases.

In heart diseases, such as heart failure, cardiac hypertrophy, abnormal heart rate, or valvular disease, a method for treating lesions accompanying diseases, i.e., a nosotropic treatment, also is mainly used. For example, a prevention of cardiac hypertrophy caused by an antihypertensive agent, or a dietary treatment, kinesitherapy or the like is used. Because heart diseases also are accompanied by hypertension, and because hypertension is believed to be one of the factors that aggravate heart diseases, antihypertensive agents are often used. Of the antihypertensive agents, in many cases those that inhibit the production or function of angiotensin II are used. This is because angiotensin II is believed to be a factor aggravating heart diseases, as it raises the blood pressure and accelerates the growth of interstitial cells in the heart, and an elimination of such a factor, insofar as possible, is believed to alleviate heart diseases.

Specifically, J. Clin. Pharmacol., 30: 155 to 158, 1990 reports that, when an antihypertensive agent (for example, Enalapril or Captopril) which is an inhibitor of an angiotensin converting enzyme inhibitor (ACEI), that is, a substance inhibiting an enzyme which converts angiotensin I to angiotensin II exhibiting a pressor function, i.e., angiotensin converting enzyme (ACE), is used, the blood pressure is lowered and the progress of the kidney diseases is ameliorated. U.S. Pat. No. 5,071,867 discloses that kidney diseases of a rat having kidney diseases were ameliorated by administering an antihypertensive agent at a dose higher than a usual dose used for lowering blood pressure, and this suggests that, if a dose is carefully and gradually increased, humans could tolerate a high dose and enjoy a benefit of treatment of kidney diseases. However, the necessity of careful administration is pointed out, because of side effects, such as a non-productive cough, which are characteristics of such kinds of medicaments, or because of a risk of acute heart failure accompanying a lowered blood pressure [Saishin-Igaku (Latest Medicine), 48: 1404 to 1409, 1993].

Subsequently, angiotensin II receptor antagonists (AGIIRA) are developed as an antihypertensive agent. Two subtypes of the angiotensin II receptors are known; subtype 1 and the subtype 2. Although a function exhibited by the subtype 2 has not been fully elucidated, it has been found that the receptor subtype 1 takes part in the blood pressure. Therefore, an antagonist against the receptor subtype 1 is a goal of the development of an antihypertensive agent.

As the antihypertensive agent which exhibits a strong antagonist function against the angiotensin II receptor, an imidazole derivative, 2-butyl-4-chloro-5-(hydroxymethyl)-1-[[2'-(1H-tetrazole-5-yl)biphenyl-4-yl]methyl]imidazole (DuP753 or MK954) is known, and its function on kidney diseases also investigated. When the imidazole derivative is administered to a rat suffering from a kidney disease, it is effective in proteinuria and glomerulosclerosis, but accompanied by an explicit lowering of the blood pressure (J. Clinical Invest., 90: 766–771, 1992). Further, when the imidazole derivative is administered to a rat suffering from hyperlipemia, renal lesion is improved without a substantial influence on the blood pressure at a lower dose, but an explicit lowering of the blood pressure is accompanied by a higher dose, which is more effective in the renal lesion (Nephron, 65: 426–432, 1993).

Compounds having structures similar to that of the imidazole derivative are disclosed in, for example, Japanese Unexamined Patent Publication (Kokai) No. 63-23868, and U.S. Pat. Nos. 5,153,197, 5,128,355 and 5,155,118. More particularly, Japanese Unexamined Patent Publication (Kokai) No. 63-23868 discloses that the imidazole derivatives are effective in hypertension and congestive heart failure; U.S. Pat. No. 5,153,197 discloses that the imidazole derivatives are effective in hypertension; U.S. Pat. No. 5,128,355 discloses that the imidazole derivatives are effective in heart failure; and U.S. Pat. No. 5,155,118 discloses that the imidazole derivatives are effective in renal insufficiency caused by a non-steroid anti-inflammatory drugs. However, they are characterized by a strong angiotensin II receptor antagonist function, and exhibit a function of lowering a blood pressure.

Compounds having a benzimidazole skeleton are disclosed in, for example, Japanese Unexamined Patent Publication (Kokai) No. 4-364171 as those effective in hypertension, heart failure, cerebral apoplexy, nephritis or the like. Further, Japanese Unexamined Patent Publication (Kokai) No. 4-346978 and U.S. Pat. No. 4,880,804 disclose angiotensin II receptor antagonists having a benzimidazole skeleton. However, these compounds exhibit a strong angiotensin II receptor antagonist function, and are characterized by a pressure-lowering function. As above, the benzimidazole compounds have the function to lower the blood pressure on the basis of the subtype 1 receptor antagonist function. Therefore, an administration to a subject suffering from kidney diseases may possibly cause acute renal insufficiency or the like.

Heart failure is the terminal stage in heart diseases, and shows progressive symptoms. A survival rate for 5 years is 50%, and the prognosis is very bad. Methods for treating heart failure are distinguished between an acute phase and a chronic phase.

In the acute phase, a cataplectic failure of a cardiac pumping function is mainly coped with, and thus a treatment to administer a cardiac is mainly carried out. In the chronic phase, a treatment to retard the progress of the symptom, or to maintain the quality of life (QOL) is used. However, if the cardiac is administered as in the treatment for the acute phase, the therapeutic effectiveness is not reliable and in many cases the prognosis becomes worse. It has been found up to now that only the angiotensin converting enzyme inhibitor can improve the prognosis. However, when the angiotensin converting enzyme inhibitor is used, the blood pressure is lowered, and side effects, such as a nonproductive cough and acute heart failure, may be caused.

As above, hitherto in the treatment of the kidney diseases or heart diseases, an agent having an as strong as possible pressure-lowering function is fundamentally desirable. In kidney diseases or heart diseases, the hypertension is an important symptom to be alleviated, but a mere lowering of the blood pressure is not sufficient. It is important to maintain an appropriate blood pressure, and thus, it is necessary to adjust the blood pressure by combining the kinds and doses of the antihypertensive agents in accordance with the symptoms. Nevertheless, a continuous treatment with a sufficient dose is required for kidney diseases or heart diseases per se. Therefore, as long as a conventional antihypertensive agent is used, it is fundamentally impossible to appropriately adjust the blood pressure, and at the same time, to effectively cure a kidney disease by the antihypertensive agent alone. One such problem is, for example, an acute renal failure caused by the antihypertensive agent used.

The inventors of the present invention carried out intensive studies to find compounds providing a sufficiently effective alleviation of the renal dysfunction or heart disease without any function to the blood pressure, and as a result, found novel benzimidazole derivatives which provide a sufficient effect in the alleviation of the renal dysfunction or heart disease, while the antagonism thereof to the angiotensin II receptor subtype 1 is one-hundredth (1/100) to one-thousandth (1/1000) or less that of the conventional antagonist having a standard activity as an antihypertensive agent, that is, there is no substantial antagonism. The present invention is based on this finding.

DISCLOSURE OF INVENTION

The present invention relates to a benzimidazole derivative of the general formula (I)

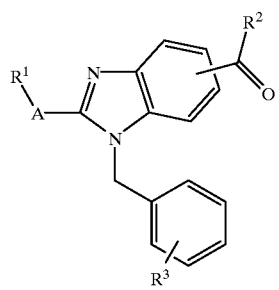

(I)

wherein A is —O— or —NH—;

$R^1$ is an aliphatic hydrocarbon group having 1 to 8 carbon atoms, or an aliphatic hydrocarbon group having 1 to 8 carbon atoms which is substituted with one or more halogen atoms;

$R^2$ is —OH, —OR$^{10}$, —NHR$^{11}$, —NR$^{12}$R$^{13}$, or —NH$_2$, or a three- to seven-membered saturated cycloaliphatic amino group which may be optionally interrupted by one or more nitrogen, oxygen, or sulfur atoms, or a three- to seven-membered saturated cycloaliphatic hydrocarbon group containing at least one nitrogen atom in the ring which is substituted with one or more aliphatic hydrocarbon groups having 1 to 8 carbon atoms, or a three- to seven-membered saturated cycloaliphatic hydrocarbon group containing at least one nitrogen atom in the ring which is substituted with one or more aliphatic hydrocarbon groups having 1 to 8 carbon atoms which is substituted with one or more halogen atoms;

$R^3$ is —COOH, —COOR$^4$, or —OH;

$R^4$ is an aliphatic hydrocarbon group having 1 to 8 carbon atoms, an aliphatic hydrocarbon group having 1 to 8 carbon atoms which is substituted with one or more halogen atoms, —(CH$_2$)$_m$NR$^{14}$R$^{15}$, —(CH$_2$)$_n$R$^5$, —(CH$_2$)$_p$CH(NR$^{16}$R$^{17}$)COOR$^{18}$, —R$^6$—COOR$^{19}$, —CH(R$^{20}$)OC(=O)R$^7$, or —CH(R$^{21}$)OC(=O)OR$^8$;

$R^5$ is a three- to seven-membered saturated cycloaliphatic amino group which may be optionally interrupted by one or more nitrogen, oxygen, or sulfur atoms, or a three- to seven-membered saturated cycloaliphatic hydrocarbon group containing at least one nitrogen atom in the ring which is substituted with one or more aliphatic hydrocarbon groups having 1 to 8 carbon atoms, or a three- to seven-membered saturated cycloaliphatic hydrocarbon group containing at least one nitrogen atom in the ring which is substituted with one or more aliphatic hydrocarbon groups having 1 to 8 carbon atoms which is substituted with one or more halogen atoms, or a three- to seven-membered unsaturated heterocyclic group;

$R^6$ is a three- to seven-membered saturated cycloaliphatic hydrocarbon group containing at least one nitrogen atom in the ring which may be optionally substituted with one or more aliphatic hydrocarbon groups having 1 to 8 carbon atoms, or a three- to seven-membered saturated cycloaliphatic hydrocarbon group containing at least one nitrogen atom in the ring which may be optionally substituted with one or more aliphatic hydrocarbon groups having 1 to 8 carbon atoms which is substituted with one or more halogen atoms;

$R^7$ and $R^8$ are —(CH$_2$)$_r$R$^9$;

$R^9$ is a hydrogen atom, an aliphatic hydrocarbon group having 1 to 8 carbon atoms, an aliphatic hydrocarbon group having 1 to 8 carbon atoms which is substituted with one or more halogen atoms, or —NR$^{22}$R$^{23}$;

$R^{10}, R^{11}, R^{12}, R^{13}, R^{14}, R^{15}, R^{16}, R^{17}, R^{18}, R^{19}, R^{22}$, and $R^{23}$ are independently an aliphatic hydrocarbon group having 1 to 8 carbon atoms, or an aliphatic hydrocarbon group having 1 to 8 carbon atoms which is substituted with one or more halogen atoms;

$R^{20}$ and $R^{21}$ are a hydrogen atom, an aliphatic hydrocarbon group having 1 to 8 carbon atoms, or an aliphatic hydrocarbon group having 1 to 8 carbon atoms which is substituted with one or more halogen atoms; and m, n, p, and r are 0 or an integer of 1 to 6, or a salt thereof.

Further, the present invention relates to a pharmaceutical composition comprising a compound of the general formula (I) or a pharmaceutically acceptable salt thereof, and a pharmaceutically acceptable carrier or diluent.

Still further, the present invention relates to a compound of the general formula (I) or a pharmaceutically acceptable salt thereof for use as a medicament for human or other mammal. Still further, the present invention relates to a compound of the general formula (I) or a pharmaceutically acceptable salt thereof for use in a medical or veterinary treatment or prevention.

Still further, the present invention relates to a use of a compound of the general formula (I) or a pharmaceutically acceptable salt thereof in the preparation of a pharmaceutical composition.

Still further, the present invention relates to a method for treating or preventing kidney diseases or heart diseases, comprising administering to an individual in need thereof an effective amount of a compound of the general formula (I) or a pharmaceutically acceptable salt thereof.

BEST MODE FOR CARRYING OUT THE INVENTION

The present invention will be explained in detail hereinafter.

The "aliphatic hydrocarbon group" includes saturated or unsaturated straight-chain, branched, or cyclic hydrocarbon groups. The saturated or unsaturated straight-chain or branched hydrocarbon groups are, for example, alkyl groups, alkenyl groups, or alkynyl groups, preferably alkyl groups. The saturated or unsaturated cyclic hydrocarbon groups are, for example, cycloalkyl groups, cycloalkenyl groups, or cycloalkynyl groups, preferably cycloalkyl groups.

An alkyl group of 1 to 8 carbon atoms is, for example, methyl, ethyl, n-propyl, i-propyl, n-butyl, i-butyl, s-butyl, t-butyl, n-pentyl, i-pentyl, neopentyl, t-pentyl, 1-methylbutyl, 2-methylbutyl, 1,2-dimethylpropyl, 1-ethylpropyl,n-hexyl, i-hexyl, 2-ethylbutyl, n-heptyl, 5-methylhexyl, n-octyl, or 4-ethylhexyl.

An alkenyl group of 2 to 8 carbon atoms is, for example, vinyl, allyl, 1-propenyl, isopropenyl, 1-butenyl, 2-butenyl, 3-butenyl, 1-methyl-1-propenyl, 2-methyl-1-propenyl, 1-methylallyl, 2-methylallyl, 1-pentenyl, 2-pentenyl, 3-pentenyl, 4-pentenyl, 1-methyl-1-butenyl, 1-methyl-2-butenyl, 1-methyl-3-butenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethylallyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, or 7-octenyl group.

An alkynyl group of 2 to 8 carbon atoms is, for example, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, or 7-octynyl group.

An cycloalkyl group of 3 to 8 carbon atoms is, for example, cyclopropyl, cyclobutyl, cyclopentyl, cyclohexyl, cycloheptyl, or cyclooctyl group. An cycloalkenyl group of 3 to 8 carbon atoms is, for example, cyclopropenyl, cyclobutenyl, cyclopentenyl, cyclohexenyl, cycloheptenyl, or cyclooctenyl group. An cycloalkynyl group of 3 to 8 carbon atoms is, for example a cyclooctynyl group.

The aliphatic hydrocarbon group having 1 to 8 carbon atoms which is substituted with one or more halogen atoms is the above aliphatic hydrocarbon group having 1 to 8 carbon atoms which is substituted with 1 to 17 halogen atoms at one or more positions possible on the basis of the number of available bonding sites. The halogen atom is, for example, a chlorine, bromine, fluorine, or iodine atom. The preferred aliphatic hydrocarbon group having 1 to 8 carbon atoms which is substituted with one or more halogen atoms is a haloalkyl group having 1 to 8 carbon atoms, such as trifluoromethyl, pentafluoroethyl, or 4,4,4-trifluorobutyl group.

The three- to seven-membered saturated cycloaliphatic amino group which may be optionally interrupted by one or more nitrogen, oxygen, or sulfur atoms is an alkyleneamino group which may be optionally interrupted by a hetero atom such as nitrogen, oxygen, or sulfur atom, for example, 1-azetidinyl, 1-pyrrolidinyl, piperidino, morpholino, thiomorpholino, or 1-piperazinyl group.

The three- to seven-membered saturated cycloaliphatic hydrocarbon group containing at least one nitrogen atom in the ring which is substituted with one or more aliphatic hydrocarbon groups having 1 to 8 carbon atoms is a three- to seven-membered saturated cycloaliphatic hydrocarbon group which is substituted with one or more aliphatic hydrocarbon groups having 1 to 8 carbon atoms and contains at least one nitrogen atom in the ring, i.e., a three- to seven-membered saturated N heterocyclic group.

The three- to seven-membered saturated cycloaliphatic hydrocarbon group containing at least one nitrogen atom in the ring which is substituted with one or more aliphatic hydrocarbon groups having 1 to 8 carbon atoms which is substituted with one or more halogen atoms is a three- to seven-membered saturated cycloaliphatic hydrocarbon group which is substituted with one or more aliphatic hydrocarbon groups having 1 to 8 carbon atoms substituted with one or more halogen atoms and contains at least one nitrogen atom in the ring, i.e., a three- to seven-membered saturated N heterocyclic group.

A three- to seven-membered cycloalkyl group containing at least one nitrogen atom in the ring which is substituted with one or more aliphatic hydrocarbon groups having 1 to 8 carbon atoms, or a three- to seven-membered cycloalkyl group containing at least one nitrogen atom in the ring which is substituted with one or more aliphatic hydrocarbon groups having 1 to 8 carbon atoms which is substituted with one or more halogen atoms is, for example, 1-methylaziridinyl, 1-methylazetidinyl, 1-methylpyrrolidinyl, 1-ethylpyrrolidinyl, 1-propylpyrrolidinyl, 3-methylimidazolidin-4-yl, 1-methylpyrazolidin-4-yl, 1-methylpiperidinyl, 1-ethylpiperidinyl, 1-propylpiperidinyl, 1-trifluoromethylpyrrolidinyl, 1-trifluoroethylpyrrolidinyl, 1-trifluoromethylpiperidyl, or 1-trifluoroethylpiperidyl group.

The three- to seven-membered unsaturated heterocyclic group is, for example, imidazolyl, oxazolyl, thiazolyl, pyrazolyl, isoxazolyl, isothiazolyl, triazolyl, oxadiazolyl, thiadiazolyl, tetrazolyl, oxatriazolyl, thiatriazolyl, thienyl, furyl, pyranyl, pyrrolyl, pyrazolinyl, imidazolinyl, pyridyl, pyrazinyl, pyrimidinyl, or pyridazinyl group. The three- to seven-membered saturated cycloaliphatic hydrocarbon group containing at least one nitrogen atom in the ring which may be optionally substituted with one or more aliphatic hydrocarbon groups having 1 to 8 carbon atoms is a three- to seven-membered saturated cycloaliphatic hydrocarbon group which may be optionally substituted with one or more aliphatic hydrocarbon groups having 1 to 8 carbon atoms and contains at least one nitrogen atom in the ring, i.e., a three- to seven-membered saturated N heterocyclic group. The three- to seven-membered saturated cycloaliphatic hydrocarbon group containing at least one nitrogen atom in the ring which may be optionally substituted with one or more aliphatic hydrocarbon groups having 1 to 8 carbon atoms which is substituted with one or more halogen atoms is a three- to seven-membered saturated cycloaliphatic hydrocarbon group which may be optionally substituted with one or more aliphatic hydrocarbon groups having 1 to 8 carbon atoms substituted with one or more halogen atoms and contains at least one nitrogen atom in the ring, i.e., a three- to seven-membered saturated N heterocyclic group.

The three- to seven-membered saturated cycloaliphatic hydrocarbon group containing at least one nitrogen atom in the ring which is substituted with one or more aliphatic hydrocarbon groups having 1 to 8 carbon atoms, or the three- to seven-membered saturated cycloaliphatic hydrocarbon group containing at least one nitrogen atom in the ring which is substituted with one or more aliphatic hydrocarbon groups having 1 to 8 carbon atoms which is substituted with one or more halogen atoms is, for example, 1-methylaziridinylene, 1-methylazetidinylene, 1-methylpyrrolidinylene, 1-ethylpyrrolidinylene, 1-propylpyrrolidinylene, pyrrolidinylene, 3-methylimidazolidin-4-ylene, 1-methylpyrazolidin-4-ylene, piperidilene, 1-methylpiperidilene, 1-ethylpiperidilene, 1-propylpiperidilene, 1-trifluoromethylpyrrolidinylene, 1-trifluoromethylpiperidilene, or 1-trifluoroethylpiperidilene group.

The benzimidazole derivative of the general formula (I) wherein A is —O— or —NH—;

$R^1$ is an aliphatic hydrocarbon group having 1 to 5 carbon atoms, or an aliphatic hydrocarbon group having 1 to 5 carbon atoms which is substituted with one or more halogen atoms;

$R^2$ is —OH, —OR$^{10}$, —NHR$^{11}$, —NR$^{12}$R$^{13}$, or —NH$_2$, or a three- to six-membered saturated cycloaliphatic amino group which may be optionally interrupted by one or more nitrogen, oxygen, orsulfur atoms, or a three- to six-membered saturated cycloaliphatic hydrocarbon group containing at least one nitrogen atom in the ring which is substituted with one or more aliphatic hydrocarbon groups having 1 to 4 carbon atoms, or a three- to six-membered saturated cycloaliphatic hydrocarbon group containing at least one nitrogen atom in the ring which is substituted with one or more aliphatic hydrocarbon groups having 1 to 4 carbon atoms which is substituted with one or more halogen atoms;

$R^3$ is —COOH, —COOR$^4$, or —OH;

$R^4$ is an aliphatic hydrocarbon group having 1 to 5 carbon atoms, an aliphatic hydrocarbon group having 1 to 5 carbon atoms which is substituted with one or more halogen atoms, —(CH$_2$)$_m$NR$^{14}$R$^{15}$, —(CH$_2$)$_n$R$^5$, —(CH$_2$)$_p$CH(NR$^{16}$R$^{17}$)COOR$^{18}$, —R$^6$—COOR$^{19}$, —CH(R$^{20}$)OC(=O)R$^7$, or —CH(R$^2$)OC(=O)OR$^8$;

$R^5$ is a three- to six-membered saturated cycloaliphatic amino group which may be optionally interrupted by one or more nitrogen, oxygen, or sulfur atoms, or a three- to six-membered saturated cycloaliphatic hydrocarbon group containing at least one nitrogen atom in the ring which is substituted with one or more aliphatic hydrocarbon groups having 1 to 4 carbon atoms, or a three- to six-membered saturated cycloaliphatic hydrocarbon group containing at least one nitrogen atom in the ring which is substituted with one or more aliphatic hydrocarbon groups having 1 to 4 carbon atoms which is substituted with one or more halogen atoms, or a three- to six-membered unsaturated heterocyclic group;

$R^6$ is a three- to six-membered saturated cycloaliphatic hydrocarbon group containing at least one nitrogen atom in the ring which may be optionally substituted with one or more aliphatic hydrocarbon groups having 1 to 4 carbon atoms, or a three- to six-membered saturated cycloaliphatic hydrocarbon group containing at least one nitrogen atom in the ring which may be optionally substituted with one or more aliphatic hydrocarbon groups having 1 to 4 carbon atoms which is substituted with one or more halogen atoms;

$R^7$ and $R^8$ are —(CH$_2$)$_r$R$^9$;

$R^9$ is a hydrogen atom, an aliphatic hydrocarbon group having 1 to 5 carbon atoms, an aliphatic hydrocarbon group having 1 to 5 carbon atoms which is substituted with one or more halogen atoms, or —NR$^{22}$R$^{23}$;

$R^{10}$, $R^{11}$, $R^{12}$, $R^{13}$, $R^{14}$, $R^{15}$, $R^{16}$, $R^{17}$, $R^{18}$, $R^{19}$, $R^{22}$, and $R^{23}$ are independently an aliphatic hydrocarbon group having 1 to 6 carbon atoms, or an aliphatic hydrocarbon group having 1 to 6 carbon atoms which is substituted with one or more halogen atoms;

$R^{20}$ and $R^{21}$ are a hydrogen atom, an aliphatic hydrocarbon group having 1 to 6 carbon atoms, or an aliphatic hydrocarbon group having 1 to 6 carbon atoms which is substituted with one or more halogen atoms; and m, n, p, and r are 0 or an integer of 1 to 5, or a salt thereof is preferable.

The benzimidazole derivative of the general formula (I) wherein A is —O— or —NH—;

$R^1$ is an aliphatic hydrocarbon group having 2 to 4 carbon atoms;

$R^2$ is a three- to six-membered saturated cycloaliphatic amino group which may be optionally interrupted by one or more nitrogen, oxygen, or sulfur atoms, or —OH, —OR$^{10}$, —NHR$^{11}$, —NR$^{12}$R$^{13}$, or —NH$_2$;

$R^3$ is —COOH, —COOR$^4$, or —OH;

$R^4$ is an alkyl group having 1 to 5 carbon atoms, —(CH$_2$)$_m$NR$^{14}$R$^{15}$, —(CH$_2$)$_n$R$^5$, or —CH$_2$OC(=O) R$^7$;

$R^5$ is a three- to seven-membered saturated cycloaliphatic amino group which may be optionally interrupted by one or more nitrogen, oxygen, or sulfur atoms;

$R^7$ is —(CH$_2$)$_r$CH$_3$;

$R^{10}$, $R^{11}$, $R^{12}$, $R^{13}$, $R^{14}$, and $R^{15}$ are independently an alkyl group having 1 or 2 carbon atoms;

m is 0 or an integer of 1 or 2;

n is an integer of 1 to 5; and r is 0 or an integer of 1 to 5, or a salt thereof is more preferable.

The benzimidazole derivative of the general formula (I) wherein —C(=O)R$^2$ is at 5- or 6-position of the benzimidazole ring, and $R^3$ is at 4-position of the phenyl ring, or a salt thereof is particularly preferable.

The benzimidazole derivative of the general formula (I) wherein —C(=O)$R^2$ is at 6-position of the benzimidazole ring, or a salt thereof is more particularly preferable.

The benzimidazole derivative of the general formula (I) wherein A is —O—;
$R^1$ is an alkyl group having 2 to 4 carbon atoms;
$R^2$ is a 1-pyrrolidinyl or piperidino group;
$R^3$ is —COO$R^4$;
$R^4$ is —(CH$_2$)$_n$$R^5$;
$R^5$ is a morpholino group;
n is an integer of 1 to 3;
—C(=O)$R^2$ is at 6-position of the benzimidazole ring; and $R^3$ is at 4-position of the phenyl ring, or a salt thereof is most preferable.

The salt of the benzimidazole derivative of the general formula (I) according to the present invention includes a salt with an inorganic or organic acid or a salt with an inorganic or organic base, preferably a pharmaceutically acceptable salt. As an acid addition salt, there may be mentioned, for example, hydrochloride, sulfate, methanesulfonate or p-toluenesulfonate; a salt with a dicarboxylic acid, such asoxalic, malonic, succinic, maleic or fumaric acid; or a salt with a monocarboxylic acid, such as acetic, propionic or butyric acid. The inorganic base suitable to form a salt of the benzimidazole derivative of the general formula (I) according to the present invention is, for example, a hydroxide, carbonate or bicarbonate of ammonium, sodium, lithium, calcium, magnesium or aluminum. As the salt with the organic base, there may be mentioned, for example, a salt with a mono-, di- or tri-alkylamine, such as methylamine, dimethylamine or triethylamine; a salt with a mono-, di- or tri-hydroxyalkylamine, guanidine, N-methylglucosamine or amino acid salt.

As a typical example of the benzimidazole derivative of the general formula (I) according to the present invention, the structures of Compounds No. 1 to No. 65 are shown in the following Tables 1 to 3. The compounds listed in the Tables 1 to 3 will be sometimes identified by the numbers given in the Tables 1 to 3.

In the following Tables, Me is methyl, Et is ethyl, nPr is n-propyl, nBu is n-butyl, iPr is i-propyl, cycPr is cyclopropyl, cycNC$_4$H$_8$O is morpholino, cycNC$_5$H$_{10}$ is piperidino, cycNC$_4$H$_8$ is 1-pyrrolidinyl, cycNC$_3$H$_6$ is 1-azetidinyl, 2'-cycN(Me)C$_4$H$_7$ is N-methyl-2-pyrrolidinyl, 2'-cycN(Me)C$_5$H$_9$ is N-methyl-2-piperidinyl, cycC$_6$H$_{11}$ is cyclohexyl, and cycNC$_6$H$_{12}$ is 1-perhydroazepinyl.

TABLE 1

| No. | $R^1$ | A | —C(=O)—$R^2$ | $R^3$ |
|---|---|---|---|---|
| 1 | Et | O | 6-COcycNC$_4$H$_8$O | 4-COOH |
| 2 | Et | O | 6-COcycNC$_4$H$_8$O | 4-OH |
| 3 | nPr | O | 6-COcycNC$_4$H$_8$O | 4-COOH |
| 4 | nBu | O | 6-COcycNC$_4$H$_8$O | 4-COOH |
| 5 | Et | O | 6-COcycNC$_5$H$_{10}$ | 4-COOH |
| 6 | Et | O | 6-COcycNC$_4$H$_8$ | 4-COOH |
| 7 | Et | O | 6-COcycNC$_3$H$_6$ | 4-COOH |
| 8 | Et | O | 6-CON(Et)$_2$ | 4-COOH |
| 9 | Et | O | 5-COOEt | 4-COOH |
| 10 | Et | O | 6-COOEt | 4-COOH |
| 11 | Et | O | 5-COOH | 4-COOH |
| 12 | Et | O | 6-COOH | 4-COOH |
| 13 | Et | O | 6-COcycNC$_4$H$_8$O | 4-COOCH$_2$CH$_2$N(Me)$_2$ |
| 14 | Et | O | 6-COcycNC$_4$H$_8$O | 4-COOCH$_2$CH$_2$N(Et)$_2$ |
| 15 | Et | O | 6-COcycNC$_4$H$_8$O | 4-COOMe |
| 16 | Et | O | 6-COcycNC$_4$H$_8$O | 4-COOEt |
| 17 | Et | O | 6-COcycNC$_4$H$_8$O | 4-COO(CH$_2$)$_4$CH$_3$ |

TABLE 1-continued

| No. | $R^1$ | A | —C(=O)—$R^2$ | $R^3$ |
|---|---|---|---|---|
| 18 | Et | O | 6-COcycNC$_4$H$_8$O | 4-COOCH$_2$OCO(CH$_2$)$_2$CH$_3$ |
| 19 | Et | O | 6-COcycNC$_4$H$_8$O | 4-COOCH$_2$OCO(CH$_2$)$_5$CH$_3$ |

TABLE 2

| No. | $R^1$ | A | —C(=O)—$R^2$ | $R^3$ |
|---|---|---|---|---|
| 20 | Et | NH | 6-COcycNC$_4$H$_8$O | 4-COOH |
| 21 | Et | NH | 6-COcycNC$_4$H$_8$O | 4-OH |
| 22 | nPr | NH | 6-COcycNC$_4$H$_8$O | 4-COOH |
| 23 | nBu | NH | 6-COcycNC$_4$H$_8$O | 4-COOH |
| 24 | Et | NH | 6-COcycNC$_5$H$_{10}$ | 4-COOH |
| 25 | Et | NH | 6-COcycNC$_4$H$_8$ | 4-COOH |
| 26 | Et | NH | 6-COcycNC$_3$H$_6$ | 4-COOH |
| 27 | Et | NH | 6-CON(Et)$_2$ | 4-COOH |
| 28 | Et | NH | 5-COOEt | 4-COOH |
| 29 | Et | NH | 6-COOEt | 4-COOH |
| 30 | Et | NH | 5-COOH | 4-COOH |
| 31 | Et | NH | 6-COOH | 4-COOH |
| 32 | Et | NH | 6-COcycNC$_4$H$_8$O | 4-COOCH$_2$CH$_2$N(Me)$_2$ |
| 33 | Et | NH | 6-COcycNC$_4$H$_8$O | 4-COOCH$_2$CH$_2$N(Et)$_2$ |
| 34 | Et | NH | 6-COcycNC$_4$H$_8$O | 4-COOMe |
| 35 | Et | NH | 6-COcycNC$_4$H$_8$O | 4-COOEt |
| 36 | Et | NH | 6-COcycNC$_4$H$_8$O | 4-COO(CH$_2$)$_4$CH$_3$ |
| 37 | Et | NH | 6-COcycNC$_4$H$_8$O | 4-COOCH$_2$OCO(CH$_2$)$_2$CH$_3$ |
| 38 | Et | NH | 6-COcycNC$_4$H$_8$O | 4-COOCH$_2$OCO(CH$_2$)$_5$CH$_3$ |
| 39 | iPr | O | 6-COcycNC$_4$H$_8$O | 4-COOH |
| 40 | cycPr | O | 6-COcycNC$_4$H$_8$O | 4-COOH |

TABLE 3

| No. | $R^1$ | A | —C(=O)—$R^2$ | $R^3$ |
|---|---|---|---|---|
| 41 | Et | O | 6-COcycNC$_4$H$_8$O | 4-COOCH$_2$O(C=O)CH(Me)CH$_2$CH$_3$ |
| 42 | Et | O | 6-COcycNC$_4$H$_8$O | 4-COOCH$_2$CH$_2$CycNC$_4$H$_8$O |
| 43 | Et | O | 6-COcycNC$_4$H$_8$O | 4-COOCH$_2$CH$_2$cycNC$_4$H$_8$ |
| 44 | Et | O | 6-COcycNC$_4$H$_8$O | 4-COOCH$_2$CH$_2$CH$_2$N(Et)$_2$ |
| 45 | Et | O | 6-COcycNC$_4$H$_8$O | 4-COOCH$_2$CH$_2$-2'-cycN(Me)C$_4$H$_7$ |
| 46 | Et | O | 6-COcycNC$_4$H$_8$O | 4-COOCH(Me)O(C=O)OEt |
| 47 | Et | O | 6-COcycNC$_4$H$_8$O | 4-COOCH$_2$CH$_2$N(nBu)$_2$ |
| 48 | Et | O | 6-COcycNC$_4$H$_8$O | 4-COO(CH$_2$)$_4$N(Me)$_2$ |
| 49 | Et | O | 6-COcycNC$_4$H$_8$O | 4-COOCH$_2$C(Me)$_2$CH$_2$N(Me)$_2$ |
| 50 | Et | O | 6-COcycNC$_4$H$_8$O | 4-COOCH$_2$CH$_2$N(iPr)$_2$ |
| 51 | Et | O | 6-COcycNC$_4$H$_8$O | 4-COO(CH$_2$)$_6$N(Me)$_2$ |
| 52 | Et | O | 6-COcycNC$_4$H$_8$O | 4-COOCH$_2$CH$_2$OCH$_2$CH$_2$N(Et)$_2$ |
| 53 | Et | O | 6-COcycNC$_4$H$_8$O | 4-COOCH$_2$-2'-cycN(Me)C$_5$H$_9$ |
| 54 | Et | O | 6-COcycNC$_4$H$_8$O | 4-COOCH(Me)O(C=O)OcycC$_6$H$_{11}$ |
| 55 | Et | O | 6-COcycNC$_5$H$_{10}$ | 4-COOCH$_2$CH$_2$N(Me)$_2$ |
| 56 | Et | O | 6-COcycNC$_5$H$_{10}$ | 4-COOCH$_2$CH$_2$N(Et)$_2$ |
| 57 | Et | O | 6-COcycNC$_5$H$_{10}$ | 4-COOCH$_2$CH$_2$cycNC$_4$H$_8$O |
| 58 | Et | O | 6-COcycNC$_6$H$_{12}$ | 4-COOH |
| 59 | Et | O | 6-COcycNC$_6$H$_{12}$ | 4-COOCH$_2$CH$_2$N(Me)$_2$ |
| 60 | Et | O | 6-CON(nPr)$_2$ | 4-COOH |
| 61 | Et | O | 6-COcycNC$_5$H$_{10}$ | 4-COOMe |
| 62 | Et | O | 6-COcycNC$_6$H$_{12}$ | 4-COOMe |
| 63 | Et | O | 6-CON(nPr)$_2$ | 4-COOMe |
| 64 | nPr | O | 6-COcycNC$_4$H$_8$O | 4-COOMe |
| 65 | Et | Q | 6-COcycNC$_4$H$_8$ | 4-COOCH$_2$CH$_2$N(Me)$_2$ |

The benzimidazole derivative of the general formula (I) according to the present invention may be prepared in accordance with a process which is in itself known. Typical schemes are illustrated hereinafter.

Scheme [1]

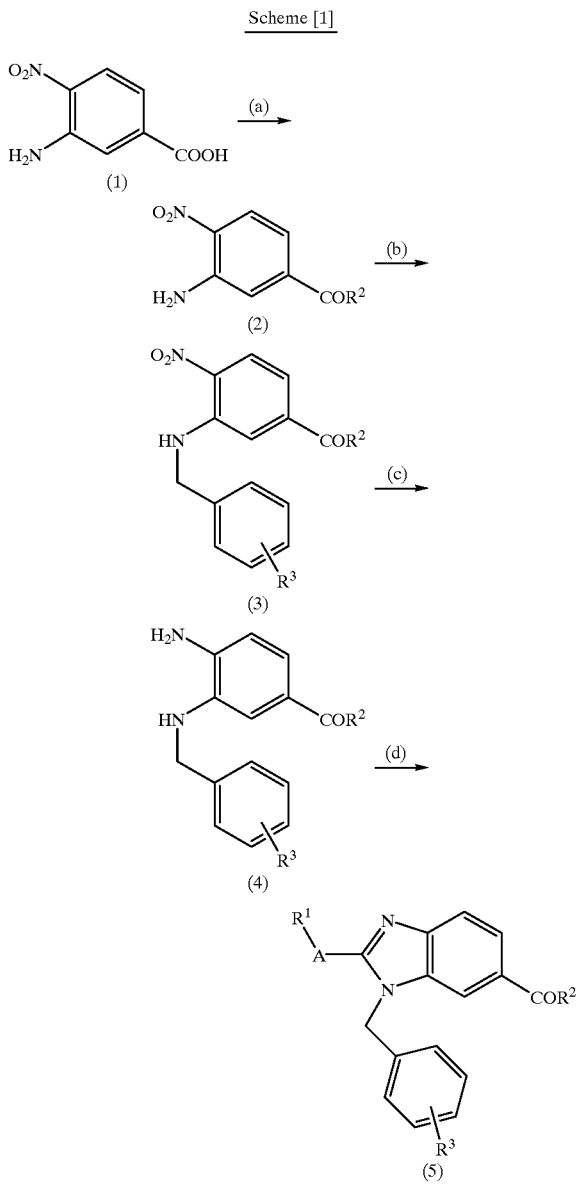

Step (a):

The compound of the general formula (1) is dissolved in an appropriate solvent, such as chloroform, tetrahydrofuran, benzene, pyridine, or N,N-dimethylformamide, and reacted with a compound capable of converting —COOH to —COR² [R² has the same meaning as above] and an appropriate condensing agent at 0 to 50° C. to obtain the compound of the general formula (2). The compound capable of converting —COOH to —COR² is, for example, morpholine when R² is a morpholino group, or may be appropriately selected in view of the desired R² group by those skilled in the art, when the R² group is a group other than the morpholino group.

Step (b):

The compound of the general formula (2) is dissolved in an appropriate solvent, such as dimethyl sulfoxide, N,N-dimethylformamide, tetrahydrofuran, t-butyl methyl ether, toluene, or benzene, and reacted with the compound of the general formula:

$$Y-CH_2-(C_6H_4)-R^3 \quad (6)$$

wherein $R^3$ has the same meaning as above, —($C_6H_4$)— is a o-phenylene group, m-phenylene group, or p-phenylene group, and Y is a leaving group, such as a halogen atom, in the presence of a base, such as diisopropylethylamine, at 20 to 110° C. to obtain the compound of the general formula (3).

Step (c):

The compound of the general formula (3) is dissolved in an appropriate solvent, such as tetrahydrofuran, alcohol, or ethyl acetate, and treated with an appropriate catalyst, such as palladium on carbon (10%), in the presence of a reducing agent, such as hydrazine hydrate, at 20° C. to a temperature below the boiling point of the solvent to obtain the compound of the general formula (4).

Step (d):

The compound of the general formula (4) is dissolved in an appropriate solvent, such as acetic acid, and reacted with a compound having a desired substituent ($R^1$—A—) and capable of forming a benzimidazole group at 20 to 140° C. to obtain the compound of the general formula (5) ($R^1$ and A have the same meanings as above). The compound having the desired substituent ($R^1$—A—) is, for example, tetra-ethoxymethane when the compound of the general formula (5) wherein $R^1$ is an ethyl group and A is an oxygen atom is prepared, or may be appropriately selected in view of the desired $R^1$ group or the A atom by those skilled in the art, when the $R^1$ or A are those other than the above group or atom. If necessary, one or more protective groups which may exist in the resulting compound can be removed by treating with an acid and/or base to obtain a free compound. After a compound wherein $R^3$ is a carboxyl group is obtained, the resulting product is treated in accordance with a conventional esterification to obtain a compound wherein $R^3$ is —$COOR^4$.

Of the benzimidazole derivatives of the general formula (I), for example, the compound wherein —C(=O)$R^2$ is at the 6-position of the benzimidazole ring, $R^3$ is at the 4-position of the phenyl ring, and $R^3$ is —$COOR^4$ may be prepared by the above process shown in Scheme [1], as well as, for example, by the following process shown in Scheme [2] comprising Steps (e) to (j).

Scheme [2]

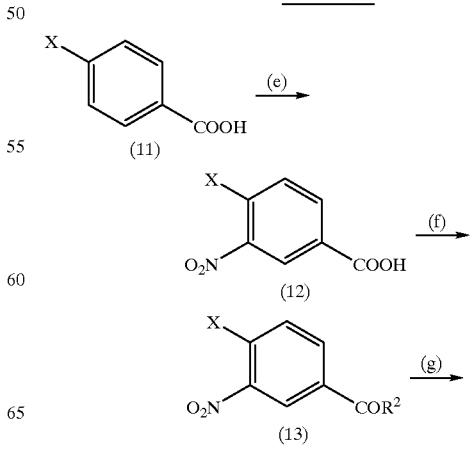

-continued

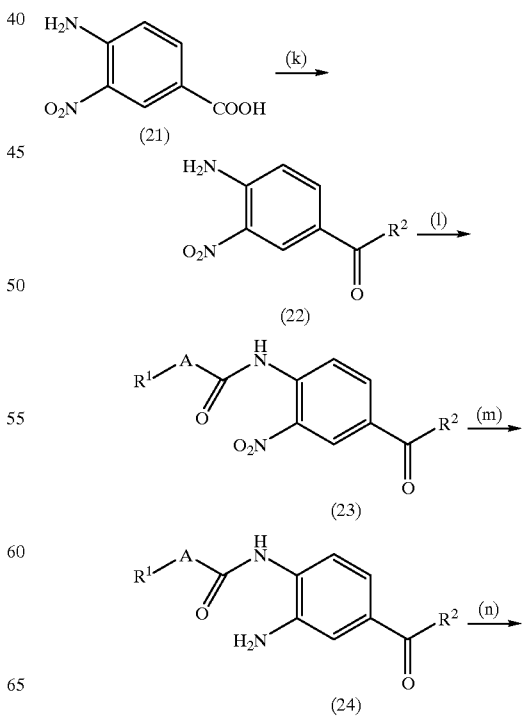

Step (e):

The compound of the general formula (11) wherein X is a halogen atom is dissolved in an appropriate solvent, such as acetic anhydride, and reacted with a compound capable of supplying nitrogen, such as fuming nitric acid, at −20 to 50° C. to obtain the compound of the general formula (12).

Step (f):

The compound of the general formula (12) is dissolved in an appropriate solvent, such as N,N-dimethylformamide, and reacted with a compound capable of converting —COOH to —COR² (R² has the same meaning as above) and an appropriate condensing agent at 0 to 50° C. to obtain the compound of the general formula (13).

Step (g):

The compound of the general formula (13) is dissolved in an appropriate solvent, such as alcohol, and reacted with an appropriate reducing agent at 20° C. to a temperature below the boiling point of the solvent to obtain the compound of the general formula (14).

Step (h):

The compound of the general formula (14) is dissolved in an appropriate solvent, such as toluene, and reacted with the compound of the general formula:

Y—CH₂—(C₆H₄)—COOR⁴    (18)

wherein R⁴ and Y have the same meanings as above, and —(C₆H₄)— is a p-phenylene group, in the presence of an appropriate base, such as diisopropylethylamine, at 20 to 110° C. to obtain the compound of the general formula (15).

Step (i):

The compound of the general formula (15) is dissolved in an appropriate solvent, such as alcohol, and reacted with a compound capable of introducing an amino group, such as ammonia, at 0 to 100° C. to obtain the compound of the general formula (16).

Step (j):

The compound of the general formula (16) is dissolved in an appropriate solvent, such as acetic acid, and reacted with a compound having a desired substituent (R¹-A-) and capable of forming a benzimidazole group at 20 to 140° C. to obtain the compound of the general formula (17) (R¹ and A have the same meanings as above). If necessary, one or more protective groups, which may exist in the resulting compound, can be removed by treating with an acid and/or base to obtain a free compound. After a compound wherein R³ is a carboxyl group is obtained, the resulting product is treated in accordance with a conventional esterification to obtain a compound wherein R³ is —COOR⁴.

Of the benzimidazole derivatives of the general formula (I), for example, the compound wherein —C(=O)R² is at the 6-position of the benzimidazole ring and R³ is at the 4-position of the phenyl ring, i.e., the compound of the formula (26) in Scheme [3], or the compound wherein —C(=O)R² is at the 5-position of the benzimidazole ring and R³ is at the 4-position of the phenyl ring, i.e., the compound of the formula (26)' in Scheme [3] may be prepared by the above process shown in Scheme [1], as well as, for example, by the following process shown in Scheme [3] comprising Steps (k) to (o).

Scheme [3]

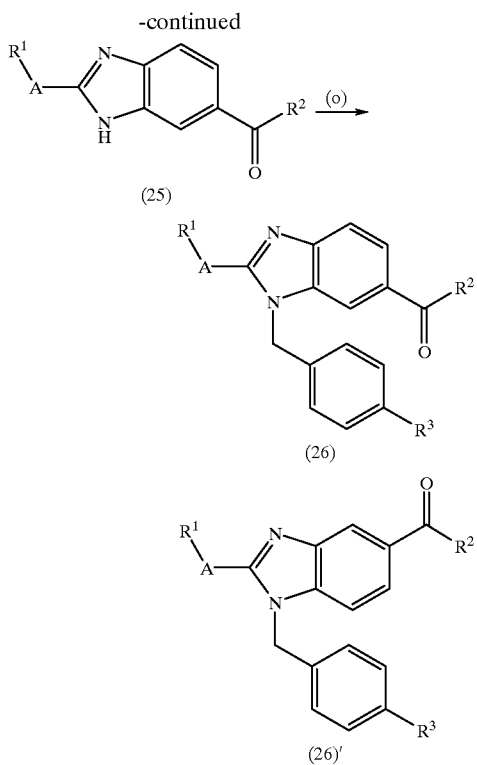

Step (k):

The compound of the formula (21) is dissolved in an appropriate solvent, such as N,N-dimethylformamide, reacted with a compound capable of converting —COOH to —COR² (R² has the same meaning as above) and an appropriate condensing agent at 0 to 50° C. to obtain the compound of the general formula (22).

Step (l):

The compound of the general formula (22) is dissolved in an appropriate solvent, such as pyridine, and reacted with a compound having a desired substituent [R¹—A—C(=O)—] at 0 to 100° C. to obtain the compound of the general formula (23) (R¹ and A have the same meanings as above). The compound having the desired substituent [R¹—A—C(=O)—] is, for example, ethyl chloroformate ester when the compound of the general formula (23) wherein R¹ is an ethyl group and A is an oxygen atom is prepared.

Step (m):

The compound of the general formula (23) is dissolved in an appropriate solvent, such as alcohol, and reacted with an appropriate reducing agent at 20° C. to a temperature below the boiling point of the solvent to obtain the compound of the general formula (24).

Step (n):

The compound of the general formula (24) is dissolved in an appropriate solvent, such as acetic acid, and a reaction is carried out at 20 to 140° C. to obtain the compound of the general formula (25).

Step (o):

The compound of the general formula (25) is dissolved in an appropriate solvent, such as N,N-dimethylformamide, and reacted with the compound of the general formula:

Y—CH₂—(C₆H₄)—R³      (27)

wherein R³ and Y have the same meanings as above, and —(C₆H₄)— is a p-phenylene group, in the presence of an appropriate base, such as potassium carbonate, at 20 to 110° C. to obtain a mixture of the compound of the general formula (26) and the compound of the general formula (26)'. If necessary, the compound of the general formula (26) and the compound of the general formula (26)' may be separated.

If necessary, one or more protective groups, which may exist in the resulting compound, can be removed by treating with an acid and/or base to obtain a free compound. After a compound wherein R³ is a carboxyl group is obtained, the resulting product is treated in accordance with a conventional esterification to obtain a compound wherein R³ is —COOR⁴.

The benzimidazole derivative of the formula (I) or the pharmaceutically acceptable salt thereof according to the present invention provides sufficiently effective therapeutic and preventive effects, particularly an alleviation of the kidney diseases, and heart diseases without any function to the blood pressure. Therefore, the present invention relates to a pharmaceutical composition, particularly an agent for treating or preventing kidney diseases (more particularly, an agent for improving or ameliorating a kidney disease) or an agent for treating or preventing heart diseases (more particularly, an agent for improving or ameliorating a heart disease), containing the benzimidazole derivative of the formula (I) or the pharmaceutically acceptable salt thereof as an active ingredient.

A derivative which may be converted to the benzimidazole derivative of the formula (I) or the pharmaceutically acceptable salt thereof in a living body, i.e., a prodrug, can be used as an active ingredient in the present invention. Methods which are generally used to select or produce appropriate prodrugs are disclosed in, for example, Design of Prodrugs, ed. H. Bundgaard, Elsevier, 1985.

The benzimidazole derivative of the formula (I) or the pharmaceutically acceptable salt thereof according to the present invention is effective as an agent for treating or preventing kidney diseases, such as nephritis, nephropathy, renal failure, nephrosis, asymptomatic proteinuria, hematuria, diabetic nephropathy, kidney diseases induced by medicine, urinary tract infectious diseases, or prostatitis.

Further, the benzimidazole derivative of the formula (I) or the pharmaceutically acceptable salt thereof according to the present invention is effective as an agent for treating or preventing heart diseases, such as left ventricular asystole (for example, myocardial infarction, dilated cardiomyopathy, or hypertensive heart disease), regurgitant valvular diseases (for example, aortic incompetence or mitral incompetence), or left and right shunt diseases (for example, patent ductus arteriosus, ventricular septal defect, or Valsalva rupture).

Further, taking into account the properties of the active ingredient, the benzimidazole derivative of the formula (I) or the pharmaceutically acceptable salt thereof according to the present invention can be applied to diseases to which the application of a conventional ACE inhibitor is avoided, for example, constrictive valvular diseases (such as, aortic stenosis or mitral stenosis), hypertrophic obstructive cardiomyopathy, or heart diseases mainly accompanied by insufficient dilation (for example, hypertrophic cardiomyopathy, constrictive pericarditis, or cardiac tamponade) or the like. In particular, hypercardia, which may be a cause of the above diseases, can be selectively treated or prevented.

The benzimidazole derivative of the formula (I) or the pharmaceutically acceptable salt thereof according to the present invention may be administered to mammals, including humans, orally or parenterally (such as percutaneously, intravenously or intraperitoneally). The benzimidazole derivative of the formula (I) or the pharmaceutically acceptable salt thereof according to the present invention were orally administered to mice at the dose of 500 mg/kg, and no fatalities were observed over a period of one week.

The benzimidazole derivative of the formula (I) or the pharmaceutically acceptable salt thereof according to the present invention may be formulated by adding one or more pharmaceutically acceptable additives to a powder, tablet, granule, capsule, suppository, injection, or oral solution. As the additives, there may be mentioned, for example, magnesium stearate, talc, lactose, dextrin, starches, methylcellulose, fatty acid glycerides, water, propyleneglycol, macrogols, alcohols, crystalline celluloses, hydroxypropylcellulose, low substituted hydroxypropylcellulose, carmelloses, povidone, polyvinylalcohol, or calcium stearate. Further, a coloring agent, stabilizer, antioxidant, preservative, pH adjusting agent, isotonicity, solubilizing agent and/or soothing agent may be contained, if necessary. The granule, tablet, or capsule may be coated with a coating base, such as hydroxypropylmethyl cellulose or hydroxypropylmethyl cellulose phthalate.

The benzimidazole derivative of the formula (I) or the pharmaceutically acceptable salt thereof according to the present invention may be contained at an amount of 0.1 to 500 mg, preferably 1 to 100 mg in a dose unit. The dose of the benzimidazole derivative of the formula (I) or the pharmaceutically acceptable salt thereof according to the present invention is 0.1 to 150 mg/kg body weight, preferably 1 to 100 mg/kg body weight. The dose may be administered once a day, or divided and given twice or 3 times a day. The dose may be appropriately selected in accordance with the symptoms of the patient.

EXAMPLES

The present invention now will be further illustrated by, but is by no means limited to, the following Examples.

Examples 1 to 6

In the following Examples 1 to 6, a benzimidazole derivative of the general formula (I) according to the present invention, 2-ethoxy-1-[[4'-(2"-N,N-dimethylaminoethoxycarbonyl)phenyl]methyl]-1H-benzimidazole-6-carboxylic acid morpholide [Compound No. 13; the compound of the formula (7a)], was prepared from 3-amino-4-nitrobenzoic acid [the compound of the formula (1a)] as a starting material in accordance with the following scheme [1a].

Scheme [1a]

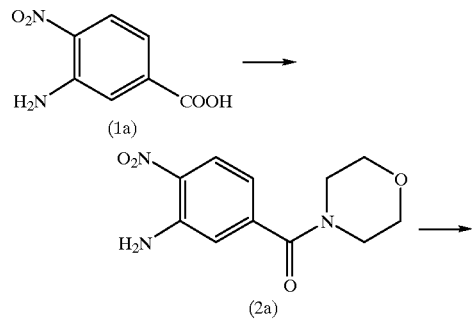

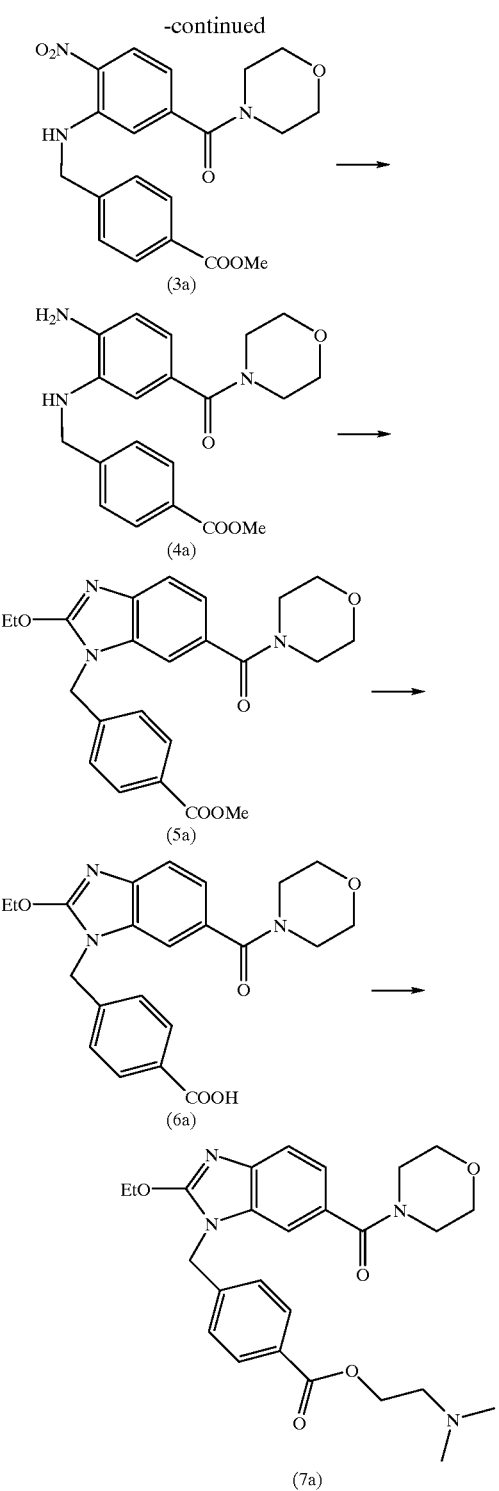

Example 1

In this Example, 3-amino-4-nitrobenzoic acid morpholide [the compound of the formula (2a)] was prepared.

In N,N-dimethylformamide (DMF) (108 ml), 3-amino-4-nitrobenzoic acid [the compound of the formula (1a)] (10.8 g) which was prepared in accordance with a known method (HECHENG HUASUE, page 91, 1995) was dissolved. Further, morpholine (10.3 ml), 1-Hydroxybenzotriazole (HOBt) (9.60 g), and 1-ethyl-3-(3-dimethylaminopropyl) carbodiimide (WSCI.HCl) (13.6 g) were successively added to the solution, and the mixture was stirred at room temperature for 18 hours. The reaction solution was poured into a 1N HCl aqueous solution to precipitate crystals, and the whole was filtrated to obtain the crystals and a filtrate. The filtrate was extracted with ethyl acetate. The resulting organic layer was dried over anhydrous sodium sulfate and concentrated under vacuum. The above crystals and the concentrate were combined to obtain 3-amino-4-nitrobenzoic acid morpholide (12.1 g; yield=81.2%) as yellow crystals.

$^1$H-NMR (500 MHz, DMSO-$d_6$) δ: 8.00 (1H, d, J=9.0 Hz), 7.51 (2H, br. s), 7.00 (1H, d, J=1.9 Hz), 6.59 (1H, dd, J=1.9, 9.0 Hz), 3.31 (8H,m)

MS (FAB): Anal. Calc'd. for $C_{11}H_{13}N_3O_4$: 251.09

Found: 252 (MH$^+$)

Example 2

In this Example, 3-N-[[(4'-methoxycarbonylphenyl) methyl]amino]-4-nitrobenzoic acid morpholide [the compound of the formula (3a)] was prepared.

In toluene (87.0 ml), 3-amino-4-nitrobenzoic acid morpholide (8.70 g) prepared in Example 1 was dissolved. Further, 4-dimethylaminopyridine (DMAP) (0.846 g), diisopropylethylamine (11.8 ml), and 4-bromomethylbenzoic acid methyl ester (9.52 g) were successively added to the solution, and the mixture was stirred at 110° C. for 20 hours. The reaction solution was poured into a 0.5N HCl aqueous solution. The whole was extracted with chloroform. An organic layer was dried over anhydrous sodium sulfate and concentrated under vacuum. The resulting crude product was purified by silica gel chromatography (chloroform: acetone=10:1) to obtain 3-N-[[(4'-methoxycarbonylphenyl) methyl]amino]-4-nitrobenzoic acid morpholide (12.64 g; yield=91.6%) as yellow crystals.

$^1$H-NMR (500 MHz, CDCl$_3$) δ: 8.52 (1H, t, J=5.5 Hz), 8.25 (1H, d, J=8.7 Hz), 8.03 (2H, d, J=8.2 Hz), 7.51 (2H, br. s), 7.40 (2H, d, J=8.2 Hz), 6.71 (1H, d, J=1.4 Hz), 6.68 (1H, dd, J=1.4, 8.7 Hz), 4.64 (2H, d, J=5.5 Hz), 3.92 (3H, s), 3.70 (4H, m), 3.39 (2H, m), 3.16 (2H, m)

MS (FAB): Anal. Calc'd. for $C_{20}H_{21}N_3O_6$: 399.14

Found: 400 (MH$^+$)

Example 3

In this Example, 4-amino-3-N-[[(4'-methoxycarbonylphenyl)-methyllamino]benzoic acid morpholide [the compound of the formula (4a)] was prepared.

In ethanol (16.15 ml), 3-N-[[(4'-methoxycarbonylphenyl)-methyl]amino]-4-nitrobenzoic acid morpholide (322.9 mg) prepared in Example 2 was dissolved. Further, palladium on carbon (10%) (32.3 mg) and hydrazine hydrate (0.333 ml) were successively added to the solution, and the mixture was stirred at 50° C. for 1 hour. The reaction solution was filtrated, and then the filtrate was concentrated under vacuum. The resulting crude product was purified by silica gel chromatography (chloroform to chloroform: acetone=3:1) to obtain 4-amino-3-N-[[(4'-methoxycarbonylphenyl)methyl]-amino]benzoic acid morpholide (145.8 mg; yield=48.8%) as an orange solid.

$^1$H-NMR (500 MHz, CDCl$_3$) δ: 8.01 (2H, d, J=8.2 Hz), 7.44 (2H, d, J=8.2 Hz), 6.80 (1H, dd, J=1.8, 7.8 Hz), 6.73 (1H, d, J=7.8 Hz), 6.63 (1H, d, J=1.8 Hz), 4.42 (2H, s), 3.92 (3H, s), 3.70–3.45 (8H, m)

MS (FAB): Anal. Calc'd. for $C_{20}H_{23}N_3O_4$: 369.17

Found: 370 (MH$^+$)

Example 4

In this Example, 2-ethoxy-1-[(4'-methoxycarbonylphenyl)-methyl]-1H-benzimidazole-6-carboxylic acid morpholide [Compound No. 15; the compound of the formula (5a)] was prepared.

To 4-amino-3-N-[[(4'-methoxycarbonylphenyl)methyl] amino] benzoic acid morpholide (145.8 mg) prepared in Example 3, tetraethoxymethane (127.3 µl) and acetic acid (22.6 µl) were successively added, and the mixture was stirred at 90° C. for 1 hour. Distilled water was added to the reaction solution, and then the whole was extracted with chloroform. An organic layer was dried over anhydrous sodium sulfate and concentrated under vacuum. The resulting crude product was purified by silica gel chromatography (chloroform:ethyl acetate=1:3 to chloroform: acetone=2:1) to obtain 2-ethoxy-1-[(4'-methoxycarbonylphenyl)methyl]-1H-benzimidazole-6-carboxylic acid morpholide (96.1 mg; yield=57.5%) as a brown solid.

$^1$H-NMR (500 MHz, CDCl$_3$) δ: 7.98 (2H, d, J=8.2 Hz), 7.53 (1H, d, J=8.2 Hz), 7.26 (2H, d, J=8.2 Hz), 7.21 (1H, dd, J=1.4, 8.2 Hz), 7.18 (1H, d, J=1.4 Hz), 5.22 (2H, s), 4.66 (2H, q, J=7.1 Hz), 3.90 (3H, s), 3.78–3.42 (8H, m), 1.48 (3H, t, J=7.1 Hz)

MS (FAB): Anal. Calc'd. for $C_{23}H_{25}N_3O_5$: 423.18

Found: 424 (MH$^+$)

Example 5

In this Example, 2-ethoxy-1-[(4'-carboxyphenyl)methyl]-1H-benzimidazole-6-carboxylic acid morpholide [Compound No. 1; the compound of the formula (6a)] was prepared.

In ethanol (6.08 ml), 2-ethoxy-1-[(4'-methoxycarbonylphenyl)methyl]-1H-benzimidazole-6-carboxylic acid morpholide (608.0 mg) prepared in Example 4 was dissolved. Further, a 1N NaOH aqueous solution (6.08 ml) was added to the solution, and the mixture was stirred at room temperature for 1 hour. The reaction solution was acidified with a 1N HCl aqueous solution, and then the whole was extracted with chloroform. An organic layer was dried over anhydrous sodium sulfate and concentrated under vacuum to obtain 2-ethoxy-1-[(4'-carboxyphenyl)methyl]-1H-benzimidazole-6-carboxylic acid morpholide (96.1 mg; yield =85.7%) as a light brown solid.

$^1$H-NMR (500 MHz, CDCl$_3$) δ: 7.93 (2H, d, J=8.4 Hz), 7.55 (1H, d, J=8.2 Hz), 7.39 (1H, d, J=1.5 Hz), 7.21 (2H, d, J=8.4 Hz), 7.21 (1H, dd, J=1.5, 8.2 Hz), 5.24 (2H, s), 4.66 (2H, q, J=7.1 Hz), 3.80 to 3.50 (8H, m), 1.45 (3H, t, J=7.1 Hz)

MS (FAB): Anal. Calc'd. for $C_{22}H_{23}N_3O_5$: 409.16

Found: 410 (MH$^+$)

Example 6

In this Example, 2-ethoxy-1-[[4'-(2"-N,N-dimethylamino-ethoxycarbonyl)phenyl]methyl]-1H-benzimidazole-6-carboxylic acid morpholide [Compound No. 13; the compound of the formula (7a)] was prepared.

In DMF (6.08 ml), 2-ethoxy-1-[(4'-carboxyphenyl) methyl]-1H-benzimidazole-6-carboxylic acid morpholide (503.9 mg) prepared in Example 5 was dissolved. Further, WSCI.HCl (354 mg), DMAP (226 mg), and dimethylaminoethanol (0.370 ml) were successively added, and the mixture was stirred at room temperature for 15.5 hours.

Distilled water was added to the reaction solution, and then the whole was extracted with chloroform. The resulting crude product was purified by silica gel chromatography (chloroform: methanol=30:1) to obtain 2-ethoxy-1-[[4,-(2"-N,N-dimethylamino-ethoxycarbonyl)-phenyl]methyl]-1H-benzimidazole-6-carboxylic acid morpholide (224 mg; yield=37.9%) as a light brown solid.

$^1$H-NMR (500 MHz, CDCl$_3$) δ: 7.99 (2H, d, J=8.4 Hz), 7.53 (1H, d, J=8.1 Hz), 7.25 (2H, d, J=8.4 Hz), 7.21 (1H, dd, J=1.5, 8.1 Hz), 7.21 (1H, d, J=1.5 Hz), 5.22 (2H, s), 4.66 (2H, q, J=7.1 Hz), 4.41 (2H, t, J=5.8 Hz), 3.85–3.35 (8H, m), 2.70 (2H, t, J=5.8 Hz), 2.32 (6H, s), 1.48 (3H, t, J=7.1 Hz)

MS (FAB): Anal. Calc'd. for $C_{26}H_{32}N_4O_5$: 480.24
Found: 481 (MH$^+$)

Examples 7 to 21

In the following Examples 7 to 21, benzimidazole derivatives of the general formula (I) according to the present invention [Compounds Nos. 41 to 54 and 16; the compounds of the formula (7b)] were prepared by esterification of 2-ethoxy-1-[(4'-carboxyphenyl)methyl]-1H-benzimidazole-6-carboxylic acid morpholide [Compound No. 1; the compound of the formula (6a)] in accordance with the following scheme [1b].

Scheme [1b]

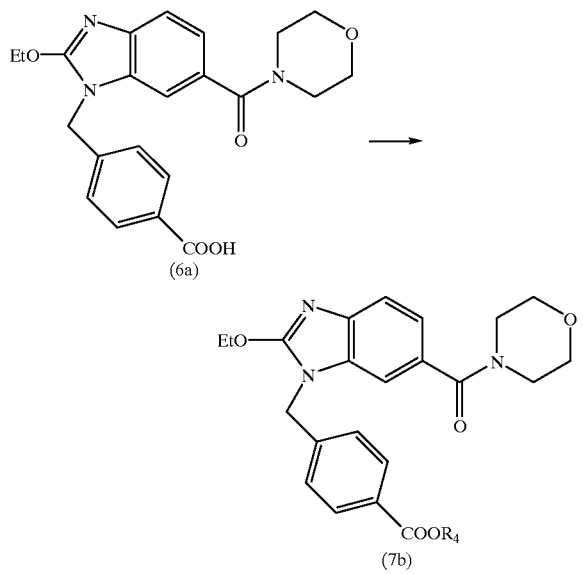

Example 7

In this Example, 2-ethoxy-1-[[4'-(1"-methyl)-butyroyloxymethoxycarbonylphenyl]methyl]-1H-benzimidazole-6-carboxylic acid morpholide [Compound No. 41] was prepared.

In DMF (12.62 ml), 2-ethoxy-1-[(4'-carboxyphenyl)methyl]-1H-benzimidazole-6-carboxylic acid morpholide (630.8 mg) prepared in Example 5 was dissolved. Further, potassium carbonate (425.9 mg), potassium iodide (127.9 mg), and chloromethyl sec-pentanoate (277.3 mg) were successively added to the solution, and the mixture was stirred at 60° C. for 1 hour. Distilled water was added to the reaction solution, and then the whole was extracted with chloroform. The resulting organic layer was dried over anhydrous sodium sulfate and concentrated under vacuum. The crude product was purified by silica gel chromatography (chloroform: acetone=4:1) to obtain 2-ethoxy-1-[[4'-(1"-methyl)-butyroyloxymethoxycarbonylphenyl]methyl]-1H-benzimidazole-6-carboxylic acid morpholide (317.4 mg; yield=39.4%) as a light brown solid.

$^1$H-NMR (60 MHz, CDCl$_3$) δ: 0.66–1.83 (11H, m), 2.13–2.63 (1H, m), 3.23–3.76 (8H, m), 4.63 (2H, q, J=6.5 Hz), 5.20 (2H, s), 5.96 (2H, s), 5.96 (2H, s), 7.00–7.36 (4H, m), 7.50 (1H, d, J=8.0 Hz), 7.92 (2H, d, J=8.5 Hz)

MS (FAB): Anal. Calc'd. for $C_{28}H_{33}N_3O_7$: 523.23
Found: 524 (MH$^+$)

Example 8

In this Example, 2-ethoxy-1-[[4'-(2"-morpholinoethoxycarbonyl)phenyl]methyl]-1H-benzimidazole-6-carboxylic acid morpholide [Compound No. 42] was prepared.

In DMF (3.99 ml), 2-ethoxy-1-[(4'-carboxyphenyl)methyl]-1H-benzimidazole-6-carboxylic acid morpholide (199.5 mg) prepared in Example 5 was dissolved. Further, WSCI.HCl (140.1 mg), DMAP (89.3 mg), and morpholine ethanol (0.178 ml) were successively added to the solution, and the mixture was stirred at room temperature for 6 hours. Distilled water was added to the reaction solution, and then the whole was extracted with chloroform. The resulting organic layer was dried over anhydrous sodium sulfate and concentrated under vacuum. The crude product was purified by silica gel chromatography (chloroform to chloroform:methanol=30:1) to obtain 2-ethoxy-1-[[4'-(2"-morpholino-ethoxycarbonyl)-phenyl]methyl]-1H-benzimidazole-6-carboxylic acid morpholide(239.7 mg; yield=94.1%) as a light brown solid.

$^1$H-NMR (60 MHz, CDCl$_3$) δ: 1.46 (3H, t, J=6.5 Hz), 2.13–2.92 (6H, m), 3.26–3.83 (12H, m), 4.33 (2H, t, J=6.0 Hz), 4.63 (2H, q, J=6.5 Hz), 5.13 (2H, s), 6.92–7.30 (4H, m), 7.40 (1H, d, J=8.0 Hz), 7.89 (2H, d, J=8.5 Hz)

MS (FAB): Anal. Calc'd. for $C_{28}H_{34}N_4O_6$: 522.25
Found: 523 (MH$^+$)

Example 9

2-Ethoxy-1-[[4'-[2"-(1'"-pyrrolidino)ethoxycarbonyl]-phenyl]methyl]-1H-benzimidazole-6-carboxylic acid morpholide [Compound No. 43] was prepared.

In DMF (3.874 ml), 2-ethoxy-1-[(4'-carboxyphenyl)methyl]-1H-benzimidazole-6-carboxylic acid morpholide (193.7 mg) prepared in Example 5 was dissolved. Further, WSCI.HCl (136.0 mg), DMAP (86.7 mg), and piperidine ethanol (0.167 ml) were successively added to the solution, and the mixture was stirred at room temperature for 6 hours. Distilled water was added to the reaction solution, and then the whole was extracted with chloroform. The resulting organic layer was dried over anhydrous sodium sulfate and concentrated under vacuum. The crude product was purified by silica gel chromatography (chloroform to chloroform:methanol=30:1) to obtain 2-ethoxy-1-[(4'-carboxyphenyl)methyl]-1H-benzimidazole-6-carboxylic acid morpholide (136.1 mg; yield=56.8%) as a light brown solid.

$^1$H-NMR (60 MHz, CDCl$_3$) δ: 1.46 (3H, t, J=7.0 Hz), 1.66–2.09 (4H, m), 2.36–2.79 (4H, m), 2.83 (2H, t, J=7 Hz), 3.36–3.97 (8H, m), 4.30 (2H, t, J=7.0 Hz), 4.50 (2H, q, J=7.0 Hz), 5.17 (2H, s), 7.03–7.40 (4H, m), 7.53 (1H, d, J=8 Hz), 7.94 (2H, d, J=8.5 Hz)

MS (FAB): Anal. Calc'd. for $C_{28}H_{34}N4O_5$: 506.25
Found: 507 (MH$^+$)

Example 10

In this Example, 2-ethoxy-1-[[4'-(3"-N,N-diethylamino-n-propoxycarbonyl)phenyl]methyl]-1H-benzimidazole-6-carboxylic acid morpholide [Compound No. 44] was prepared.

In DMF (4.06 ml), 2-ethoxy-1-[(4'-carboxyphenyl)methyl]-1H-benzimidazole-6-carboxylic acid morpholide (202.8 mg) prepared in Example 5 was dissolved. Further, WSCI.HCl (142.4 mg), DMAP (90.8 mg), and 3,3'-diethylaminopropanol (0.222 ml) were successively added to the solution, and the mixture was stirred at room temperature for 15 hours. Distilled water was added to the reaction solution, and then the whole was extracted with chloroform. The resulting organic layer was dried over anhydrous sodium sulfate and concentrated under vacuum. The crude product was purified by silica gel chromatography (chloroform:methanol=30:1) to obtain 2-ethoxy-1-[[4'-(3'-N,N-diethylamino-n-propoxycarbonyl)-phenyl]methyl]-1H-benzimidazole-6-carboxylic acid morpholide (193.5 mg; yield=74.7%) as a light brown solid.

$^1$H-NMR (60 MHz, CDCl$_3$) δ: 1.03 (6H, t, J=7 Hz), 1.50 (3H, t, J=7 Hz), 1.69–2.20 (2H, m), 2.43 (2H, t, J=7 Hz), 2.50 (4H, q, J=7 Hz), 3.29–3.93 (8H, m), 4.33 (2H, t, J=7 Hz), 4.66 (2H, q, J=7 Hz), 5.20 (2H, s), 7.09–7.40 (4H, m), 7.52 (1H, d, J=8 Hz), 7.94 (2H, d, J=7.5 Hz)

MS (FAB): Anal. Calc'd. for C$_{29}$H$_{38}$N$_4$O$_5$: 522.28

Found: 523 (MH$^+$)

Example 11

In this Example, 2-ethoxy-1-[[4'-[2'"-(N-methyl-2'"-pyrrolidinyl)-ethoxycarbonyl]phenyl]methyl]-1H-benzimidazole-6-carboxylic acid morpholide [Compound No. 45] was prepared.

In DMF (3.942 ml), 2-ethoxy-1-[(4'-carboxyphenyl)methyl]-1H-benzimidazole-6-carboxylic acid morpholide (197.1 mg) prepared in Example 5 was dissolved. Further, WSCI.HCl (138.4 mg), DMAP (88.2 mg), and N-methyl-2-pyrrolidine ethanol (0.194 ml) were successively added to the solution, and the mixture was stirred at room temperature for 15 hours. Distilled water was added to the reaction solution, and then the whole was extracted with chloroform. The resulting organic layer was dried over anhydrous sodium sulfate and concentrated under vacuum. The crude product was purified by silica gel chromatography (chloroform:methanol=30:1) to obtain 2-ethoxy-1-[[4'-[2"-(N-methyl-2'"-pyrrolidinyl)-ethoxycarbonyl]phenyl]methyl]-1H-benzimidazole-6-carboxylic acid morpholide (167.8 mg; yield=67.0%) as a light brown solid.

$^1$H-NMR (60 MHz, CDCl$_3$) δ: 1.09–2.41 (8H, m), 1.46 (3H, t, J=7.0 Hz), 2.30 (3H, s), 2.86–3.23 (1H, m), 3.33–3.79 (8H, m), 4.33 (2H, t, J=7.0 Hz), 4.63 (2H, q, J=7.0 Hz), 5.17 (2H, s), 7.03–7.36 (4H, m), 7.46 (1H, d, J=8 Hz), 7.94 (2H, d, J=8.5 Hz)

MS (FAB): Anal. Calc'd. for C$_{29}$H$_{36}$N$_4$O$_5$: 520.27

Found: 521 (MH$^+$)

Example 12

In this Example, 2-ethoxy-1-[[4'-[1"-(ethoxycarbonyloxy)-ethoxycarbonyl]phenyl]methyl]-1H-benzimidazole-6-carboxylic acid morpholide [Compound No. 46] was prepared.

In DMF (3.412 ml), 2-ethoxy-1-[(4'-carboxyphenyl)methyl]-1H-benzimidazole-6-carboxylic acid morpholide (170.6 mg) prepared in Example 5 was dissolved. Further, potassium carbonate (69.1 mg), potassium iodide (34.6 mg), and ethyl 1-chloroethyl carbonate (66.9 μl) were added to the solution, and the mixture was stirred at 60° C. for 2.5 hours. The reaction solution was acidified with a 1N HCl aqueous solution, and then the whole was extracted with ethyl acetate. The resulting organic layer was dried over anhydrous sodium sulfate and concentrated under vacuum. The crude product was purified by silica gel chromatography (chloroform:methanol=15:1) to obtain 2-ethoxy-1-[[4'-[1"-(ethoxycarbonyloxy)-ethoxycarbonyl]phenyl]methyl]-1H-benzimidazole-6-carboxylic acid morpholide (164.5 mg; yield=75.1%) as a light brown solid.

$^1$H-NMR (60 MHz, CDCl$_3$) δ: 1.30 (3H, t, J=7.0 Hz), 1.46 (3H, t, J=7.0 Hz), 1.63 (3H, d, J=6.0 Hz), 3.17–3.79 (8H, m), 4.23 (2H, q, J=7.0 Hz), 4.66 (2H, q, J=7.0 Hz), 5.20 (2H, s), 6.97 (1H, q, J=6.0 Hz), 7.03–7.36 (4H, m), 7.53 (1H, d, J=8 Hz), 7.94 (2H, d, J=8.5 Hz)

MS (FAB): Anal. Calc'd. for C$_{27}$H$_{31}$N$_3$O$_8$: 525.21

Found: 526 (MH$^+$)

Example 13

In this Example, 2-ethoxy-1-[[4'-(2"-(n-dibutylamino)-ethoxycarbonyl)phenyl]methyl]-1H-benzimidazole-6-carboxylic acid morpholide [Compound No. 47] was prepared.

In DMF (4.0 ml), 2-ethoxy-1-[(4'-carboxyphenyl)methyl]-1H-benzimidazole-6-carboxylic acid morpholide (196.5 mg) prepared in Example 5 was dissolved. Further, WSCI.HCl (138 mg), DMAP (87.9 mg), and 2-di-n-butylaminoethanol (249.5 mg) were successively added to the solution, and the mixture was -stirred at room temperature for 22 hours. The reaction solution was poured into distilled water, and then the whole was extracted with chloroform. The resulting crude product was purified by silica gel chromatography (chloroform:methanol=30:1) to obtain 2-ethoxy-1-[[4'-(2"-(n-dibutylamino)-ethoxycarbonyl)phenyl]methyl]-1H-benzimidazole-6-carboxylic acid morpholide (182.7 mg; yield=67.4%) as a light yellow solid.

$^1$H-NMR (60 MHz, CDCl$_3$) δ: 0.6–1.8 (16H, m), 2.3–3.0 (5H, m), 2.83 (2H, t, J=6.4 Hz), 3.83 (8H, s), 4.42 (2H, t, J=6.4 Hz), 4.78 (2H, q, J=7.1 Hz), 5.23 (2H, s), 7.2–7.8 (5H, m), 8.10 (2H, d, J=8.4 Hz)

MS (FAB): Anal. Calc'd. for C$_{32}$H$_{44}$N$_4$O$_5$: 564.73

Found: 566 (MH$^+$)

Example 14

In this Example, 2-ethoxy-1-[[4'-[4"-(dimethylamino)-butoxycarbonyl]phenyl]methyl]-1H-benzimidazole-6-carboxylic acid morpholide [Compound No. 48] was prepared.

In DMF (4.0 ml), 2-ethoxy-1-[(4'-carboxyphenyl)methyl]-1H-benzimidazole-6-carboxylic acid morpholide (199.9 mg) preparedin Example 5 was dissolved. Further, WSCI.HCl (140.4 mg), DMAP (29.8 mg), and 4-dimethylamino-1-butanol (171.6 mg) were -successively added to the solution, and the mixture was stirred at room temperature for 16 hours. The reaction solution was poured into distilled water, and then the whole was extracted with chloroform. The resulting crude product was purified by silica gel chromatography (chloroform:methanol=15:1) to obtain 2-ethoxy-1-[[4'-[4"-(dimethylamino)-butoxycarbonyl]phenyl]methyl]-1H-benzimidazole-6-carboxylic acid morpholide (203 mg; yield=81.7%) as light yellow oil.

¹H-NMR (60 MHz, CDCl₃) δ: 1.0–4.0 (6H, m), 1.50 (3H, t, J=7.1 Hz), 2.23 (6H, s), 3.65 (8H, bs), 4.37 (2H, t, J=6.4 Hz), 4.72 (2H, q, J=7.1 Hz), 5.27 (2H, s), 7.2–7.7 (5H, m), 8.05 (2H, d, J=8.4 Hz)

MS (FAB): Anal. Calc'd. for C₂₈H₃₆N₄O₅: 508.62
Found: 510 (MH⁺)

Example 15

In this Example, 2-ethoxy-1-[[4'-[3"-(dimethylamino)-2",2"-dimethylpropoxycarbonyl]phenyl]methyl]-1H-benzimidazole-6-carboxylic acid morpholide [Compound No. 49] was prepared.

In DMF (4.0 ml), 2-ethoxy-1-[(4'-carboxyphenyl)methyl]-1H-benzimidazole-6-carboxylic acid morpholide (201.8 mg) prepared in Example 5 was dissolved. Further, WSCI.HCl (141.7 mg), DMAP (30.1 mg), and 3-dimethylamino-2,2-dimethyl-1-propanol (194.0 mg) were successively added to the solution, and the mixture was stirred at room temperature for 16 hours. The reaction solution was poured into distilled water, and then the whole was extracted with chloroform. The resulting crude product was purified by silica gel chromatography (chloroform:methanol=30:1) to obtain 2-ethoxy-1-[[4'-[3"-(dimethylamino)-2",2"-dimethylpropoxycarbonyl]phenyl]methyl]-1H-benzimidazole-6-carboxylic acid morpholide (185.9 mg; yield=72.2%) as a light yellow solid.

¹H-NMR (60 MHz, CDCl₃) δ: 0.98 (6H, s), 1.50 (3H, t, J=7.1 Hz), 2.28 (2H, d, J=1.2 Hz), 2.31 (6H, s), 3.65 (8H, s), 4.16

MS (FAB): Anal. Calc'd. for C₂₉H₃₈N₄O₅: 522.65
Found: 524 (MH⁺)

Example 16

In this Example, 2-ethoxy-1-[[4'-[2"-(diisopropylamino)-ethoxycarbonyl]phenyl]methyl]-1H-benzimidazole-6-carboxylicacid morpholide [Compound No. 50] was prepared.

In DMF (4 ml), 2-ethoxy-1-[(4'-carboxyphenyl)methyl]-1H-benzimidazole-6-carboxylic acid morpholide (196 mg) prepared in Example 5 was dissolved. Further, WSCI.HCl (138 mg), DMAP (88 mg), and diisopropylaminoethanol (0.25 ml) were successively added to the solution, and the mixture was reacted at room temperature for 13 hours. The reaction solution was concentrated under vacuum. To the resulting residue, 1N HCl was added, and then the whole was extracted with chloroform. An organic layer was washed with saturated brine, dried over anhydrous sodium sulfate, and concentrated under vacuum. The resulting crude product was purified by silica gel chromatography (chloroform:methanol=10:1) to obtain 2-ethoxy-1-[[4'-[2"-(diisopropylamino)ethoxycarbonyl]-phenyl]methyl]-1H-benzimidazole-6-carboxylic acid morpholide (124.9 mg; yield=48.6%) as light yellow foam.

¹H-NMR (60 MHz, CDCl₃) δ: 1.17–1.67 (15H, m), 2.90–3.50 (4H, br), 3.67 (8H, brs), 4.50–4.98 (4H, m), 5.27 (2H, s), 7.17–7.48 (4H, m), 7.62 (1H, d, J=7.5 Hz), 8.10 (2H, d, J=8.0 Hz)

MS (FAB): Anal. Calc'd. for C₃₀H₄₀N₄O₅: 536.30
Found: 537 (MH⁺)

Example 17

In this Example, 2-ethoxy-1-[[4'-[6"-(dimethylamino)-n-hexyloxycarbonyl]phenyl]methyl]-1H-benzimidazole-6-carboxylic acid morpholide [Compound No. 51] was prepared.

In DMF (4 ml), 2-ethoxy-1-[(4'-carboxyphenyl)methyl]-1H-benzimidazole-6-carboxylic acid morpholide (200 mg) prepared in Example 5 was dissolved. Further, WSCI.HCl (140 mg), DMAP (60 mg), and dimethylamino-n-hexanol (142 mg) were successively added to the solution, and the mixture was reacted at room temperature for 11 hours. The reaction solution was concentrated under vacuum. The resulting crude product was purified by silica gel chromatography (chloroform:methanol=30:1) to obtain 2-ethoxy-1-[[4'-[6"-(dimethylamino)-n-hexyloxycarbonyl]phenyl]methyl]-1H-benzimidazole-6-carboxylic acid morpholide (162.4 mg; yield=62.0%) as syrup.

¹H-NMR (60 MHz, CDCl₃) δ: 1.10–1.90 (11H, m), 2.10–2.50 (2H, m), 2.21 (6H, s), 3.68 (8H, brs), 3.50–3.90 (2H, m), 4.21–4.90 (4H, m), 5.26 (2H, s), 7.15–7.49 (4H, m), 7.60 (1H, d, J=7.5 Hz), 8.05 (2H, d, J=8.0 Hz)

MS (FAB): Anal. Calc'd. for C₃₀H₄₀N₄O₅: 536.30
Found: 537 (MH⁺)

Example 18

In this Example, 2-ethoxy-1-[[4'-[2"-[2'"-(diethylamino)ethoxy]ethoxycarbonyl]phenyl]methyl]-1H-benzimidazole-6-carboxylic acid morpholide [Compound No. 52] was prepared.

In DMF (4 ml), 2-ethoxy-1-[(4'-carboxyphenyl)methyl]-1H-benzimidazole-6-carboxylic acid morpholide (200 mg) prepared in Example 5 was dissolved. Further, WSCI.HCl (140 mg), DMAP (60 mg), and 2-[2'-(diethylamino)ethoxy]ethanol (142 mg) weresuccessively added to the solution, and the mixture was reacted at room temperature for 11 hours. The reaction solution was concentrated under vacuum. The resulting crude product was purified by silica gel chromatography (chloroform:methanol=30:1) to obtain 2-ethoxy-1-[[4'-[2"-[2'"-(diethylamino)ethoxy]ethoxycarbonyl]phenyl]methyl]-1H-benzimidazole-6-carboxylic acid morpholide (171.3 mg; yield=67.1%) as syrup.

¹H-NMR (60 MHz, CDCl₃) δ: 1.01 (6H, t, J=7.0 Hz), 1.49 (3H, t, J=7.0 Hz), 2.40–2.81 (6H, m), 3.66 (8H, brs), 4.38–4.94 (4H, m), 5.26 (2H, s), 7.18–7.46 (4H, m), 7.62 (1H, d, J=7.5 Hz), 8.09 (2H, d, J=8.0 Hz)

MS (FAB): Anal. Calc'd. for C₃₀H₄₀N₄O₆: 551.31
Found: 552 (MH⁺)

Example 19

In this Example, 2-ethoxy-1-[[4'-[(1"-methylpiperidin-2"-yl)methoxycarbonyl]phenyl]methyl]-1H-benzimidazole-6-carboxylic acid morpholide [Compound No. 53] was prepared.

In DMF (4 ml), 2-ethoxy-1-[(4'-carboxyphenyl)methyl]-1H-benzimidazole-6-carboxylic acid morpholide (200 mg) prepared in Example 5 was dissolved. Further, WSCI.HCl (140 mg), DMAP (60 mg), and 1-methylpiperidin-2-methanol (126 mg) were successively added to the solution, and the mixture was reacted at room temperature for 11 hours. The reaction solution was concentrated under vacuum. The resulting crude product was purified by silica gel chromatography (chloroform:methanol=30:1) to obtain 2-ethoxy-1-[[4'-[(1"-methyl-piperidin-2"-yl)methoxycarbonyl]phenyl]methyl]-1H-benzimidazole-6-carboxylic acid morpholide (173.0 mg; yield=68.0%) as syrup.

¹H-NMR (60 MHz, CDCl₃) δ: 1.12–1.67 (15H, m), 2.40 (3H, s), 3.68 (8H, brs), 4.38–4.90 (4H, m), 5.30 (2H, s), 7.20–7.48 (4H, m), 7.62 (1H, d, J=7.5 Hz), 8.13 (2H, d, J=8.0 Hz)

MS (FAB): Anal. Calc'd. for $C_{29}H_{36}N_4O_5$: 520.27
Found: 521 (MH$^+$)

Example 20

In this Example, 2-ethoxy-1-[[4'-[1"-(cyclohexyloxycarbonyloxy)-ethoxycarbonyl]phenyl]methyl]-1H-benzimidazole-6-carboxylic acid morpholide [Compound No. 54] was prepared.

In DMF (5.572 ml), 2-ethoxy-1-[(4'-carboxyphenyl)methyl]-1H-benzimidazole-6-carboxylic acid morpholide (278.6 mg) prepared in Example 5 was dissolved. Further, potassium carbonate (112.9 mg), potassium iodide (56.5 mg), and cyclohexyl-1-chloroethylcarbonate (281.0 mg) were added to the solution, and the mixture was stirred at 60° C. for 3 hours. The reaction solution was acidified with 1N HCl aqueous solution, and then the whole was extracted with chloroform. The resulting organic layer was dried over anhydrous sodium sulfate and concentrated under vacuum. The crude product was purified by silica gel chromatography (chloroform:acetone=3:1) to obtain 2-ethoxy-1-[[4'-[1"-(cyclohexyloxycarbonyloxy)-ethoxycarbonyl]phenyl]methyl]-1H-benzimidazole-6-carboxylic acid morpholide (166.7 mg; yield=42.3%) as a white solid.

$^1$H-NMR (500 MHz, CDCl$_3$) δ: 1.20–2.10 (10H, m), 1.50 (3H, t, J=7 Hz), 1.66 (3H, d, J=7 Hz), 3.50–3.90 (8H, m), 4.70–4.90 (1H, m), 4.76 (2H, q, J=7 Hz), 5.33 (2H, s), 7.13 (1H, q, J=7 Hz), 7.5–7.25 (4H, m), 7.69 (1H, d, J=8 Hz), 8.16 (2H, d, J=8.5 Hz)

MS (FAB): Anal. Calc'd. for $C_{31}H_{37}N_3O_8$: 579.26
Found: 580 (MH$^+$)

Example 21

In this Example, 2-ethoxy-1-[(4'-ethoxycarbonylphenyl)-methyl]-1H-benzimidazole-6-carboxylic acid morpholide [Compound No. 16] was prepared.

In DMF (12.34 ml), 2-ethoxy-1-[(4'-carboxyphenyl)methyl]-1H-benzimidazole-6-carboxylic acid morpholide (617.2 mg) prepared in Example 5 was dissolved. Further, WSCI.HCl (433.5 mg), DMAP (276.2 mg), and ethanol (0.264 ml) were successively added to the solution, and the mixture was stirred at room temperature for 1 hour. To the reaction solution, a 1N HCl aqueous solution was added, and then the whole was extracted with chloroform. The resulting organic layer was dried over anhydrous sodium sulfate and concentrated under vacuum. The crude product was purified by silica gel chromatography (chloroform:acetone=2:1) to obtain 2-ethoxy-1-[(4'-ethoxycarbonylphenyl)methyl]-1H-benzimidazole-6-carboxylic acid morpholide (438.2 mg; yield=66.4%) as a light yellow solid.

$^1$H-NMR (60 MHz, CDCl$_3$) δ: 1.40 (3H, t, J=6.5 Hz), 1.59 (3H, t, J=7.0 Hz), 3.50–3.89 (8H, m), 4.36 (2H, q, J=7.0 Hz), 4.66 (2H, q, J=6.5 Hz), 5.23 (2H, s), 7.20–7.40 (4H, m), 7.53 (1H, d, J=8.0 Hz), 8.00 (2H, d, J=8.5 Hz)

MS (FAB): Anal. Calc'd. for $C_{24}H_{27}N_3O_5$: 437.20
Found: 438 (MH$^+$)

Examples 22 to 23

In the following Examples 22 to 23, benzimidazole derivatives of the general formula (I) according to the present invention [Compound No. 6; the compound of the formula (6c), and compound No. 65; the compound of the formula (7c)] were prepared from 3-amino-4-nitrobenzoic acid [the compound of the formula (1a)] in accordance with the following scheme [1c] which is similar to the method shown in the scheme [1a].

Scheme [1c]

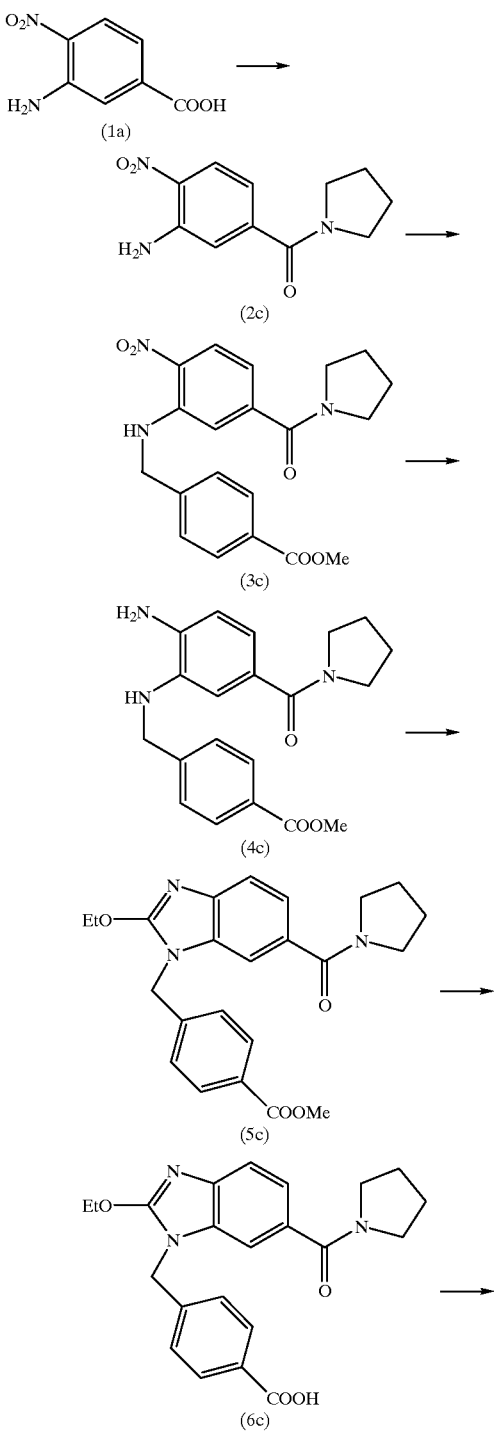

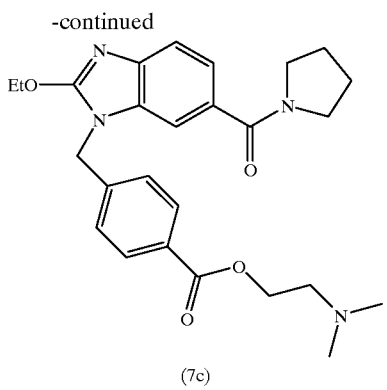

(7c)

Example 22

In this Example, 2-ethoxy-1-[(4'-carboxyphenyl)methyl]-1H-benzimidazole-6-carboxylic acid pyrrolidinamide [Compound No. 6; the compound of the formula (6c)] was prepared.

To 4-amino-3-[(4'-methoxycarbonylphenyl)methylamino]benzoic acid pyrrolidinamide[the compound of the formula (4c)] (2.11 g) obtained from 3-amino-4-nitrobenzoic acid by the method similar to that shown in the scheme [1a], acetic acid (0.35 ml) and tetraethoxymethane (1.9 ml) were successively added, and the mixture was stirred at 90° C. for 3 hours. The reaction solution was diluted with chloroform, a saturated sodium hydrogencarbonate aqueous solution was added to the solution, and then the whole was extracted with chloroform. An organic layer was dried over anhydrous sodium sulfate and concentrated under vacuum. The resulting crude product was dissolved in methanol (24 ml). Further, 1N NaOH aqueous solution (24 ml) was added, and the mixture was reacted at room temperature for 1 hour. The reaction solution was acidified with 1N HCl, and then the whole was extracted with chloroform. An organic layer was dried over anhydrous sodium sulfate and concentrated under vacuum. The resulting crude product was purified by silica gel chromatography (chloroform:methanol=20:1) to obtain 2-ethoxy-1-[(4'-carboxyphenyl)methyl]-1H-benzimidazole-6-carboxylic acid pyrrolidinamide (1.34 g; yield=56.9%) as a light yellow solid.

$^1$H-NMR (500 MHz, CDCl$_3$) δ: 1.41 (3H, t, J=7.0 Hz), 1.70–2.10 (4H, m), 3.30–3.90 (4H, m), 4.71 (2H, dd, J=7.0 Hz), 5.28 (2H, s), 7.12–7.75 (5H, m), 7.96 (2H, d, J=8.0 Hz)

MS (FAB): Anal. Calc'd. for C$_{22}$H$_{23}$N$_3$O$_4$: 393.17

Found: 394 (MH$^+$)

Example 23

In this Example, 2-ethoxy-1-[[4'-[2"-(dimethylamino)-ethoxycarbonyl]phenyl]methyl]-1H-benzimidazole-6-carboxylic acid pyrrolidinamide [Compound No. 65; the compound of the formula (7c)] was prepared.

In DMF (4 ml), 2-ethoxy-1-[(4'-carboxyphenyl)methyl]-1H-benzimidazole-6-carboxylic acid pyrrolidinamide (202.2 mg) prepared in Example 22 was dissolved. Further, WSCI.HCl (150 mg), DMAP (94 mg), and dimethylaminoethanol (77 ml) were successively added to the solution, and the mixture was stirred at room temperature for 16 hours. The reaction solution was concentrated under vacuum and dried under vacuum. The resulting crude product was purified by silica gel chromatography (chloroform:methanol= 20:1) to obtain 2-ethoxy-1-[[4'-[2"-(dimethylamino)ethoxy]carbonylphenyl]-methyl]-1H-benzimidazole-6-carboxylic acid pyrrolidinamide (154.1 mg; yield=64.5%) as yellow syrup.

$^1$H-NMR (500 MHz, CDCl$_3$) δ: 1.47 (3H, t, J=7.0 Hz), 1.70–2.20 (4H, m), 2.34 (6H, s), 2.74 (2H, t, J=6.5 Hz), 4.30–4.90 (4H, m), 5.28 (2H, s), 7.20–7.70 (5H, m), 8.08 (2H, d, J=8.0 Hz)

MS (FAB): Anal. Calc'd. for C$_{26}$H$_{32}$N$_4$O$_4$: 464.24

Found: 465 (MH$^+$)

Examples 24 to 28

In the following Examples 24 to 28, benzimidazole derivatives of the general formula (I) according to the present invention [Compound No. 61; the compound of the formula (5d), Compound No. 5; the compound of the formula (6d), and Compounds Nos. 55 to 57; the compound of the general formula (7d)] were prepared from 3-amino-4-nitrobenzoic acid [the compound of the formula (1a)] in accordance with the following scheme [1d] which is similar to the method shown in the scheme [1a].

Scheme [1d]

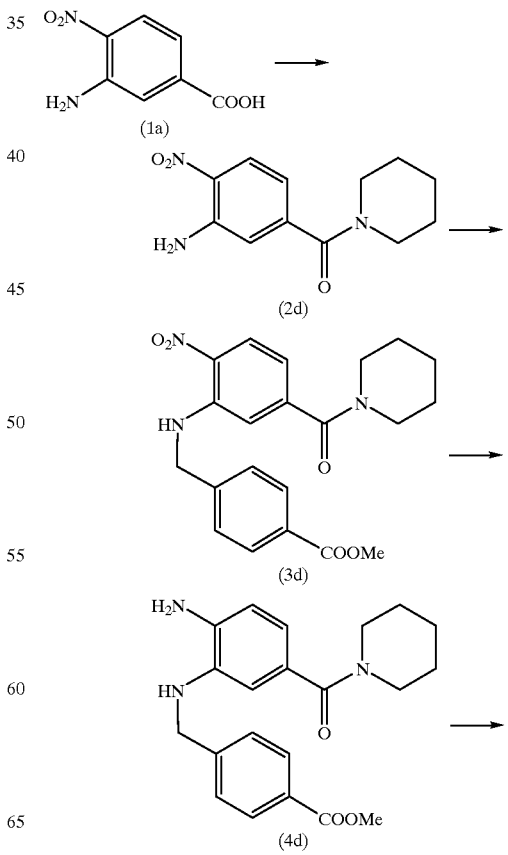

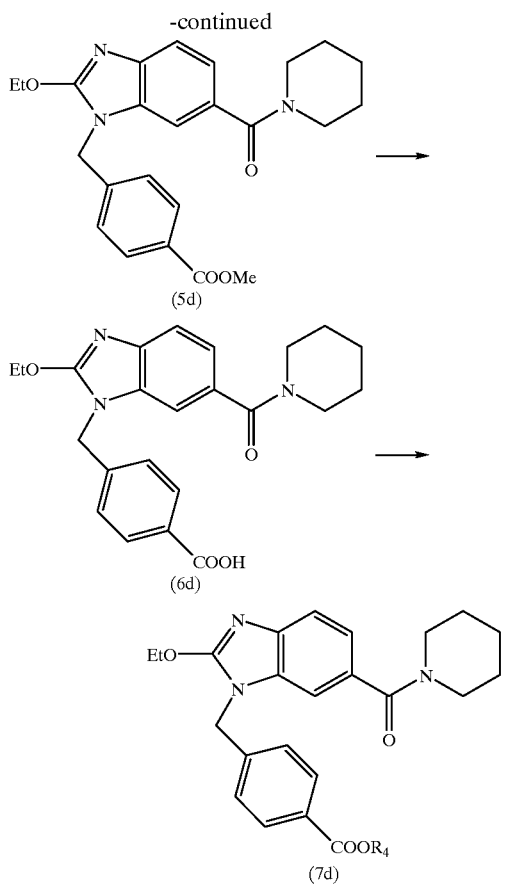

Example 24

In this Example, 2-ethoxy-1-[(4'-methoxycarbonylphenyl)-methyl]-1H-benzimidazole-6-carboxylic acid piperidinamide [Compound No. 61; the compound of the formula (5d)] was prepared.

To 4-amino-3-[(4'-methoxycarbonylphenyl)methylamino]-benzoic acid piperidinamide [the compound of the formula (4d)] (924 mg) obtained from 3-amino-4-nitrobenzoic acid by the method similar to that shown in the scheme [1a], tetraethoxymethane (810 μl) and acetic acid (144 μl) were successively added, and the mixture was stirred at 90° C. for 1 hour. Distilled water was added to the reaction solution, and then the whole was extracted with chloroform. An organic layer was dried over anhydrous sodium sulfate and concentrated under vacuum. The resulting crude product was purified by silica gel chromatography (chloroform: acetone=4:1) to obtain 2-ethoxy-1-[(4'-methoxycarbonylphenyl)methyl]-1H-benzimidazole-6-carboxylic acid piperidinamide (882 mg; yield=83.2%) as a brown solid. $^1$H-NMR (60 MHz, CDCl$_3$) δ: 1.13–2.00 (6H, m), 1.46 (3H, t, J=7.0 Hz), 3.17–3.72 (4H, m), 3.89 (3H, s), 4.67 (2H, q, J=7.0 Hz), 5.23 (2H, s), 6.97–7.43 (4H, m), 7.56 (1H, d, J=8.0 Hz), 8.00 (2H, d, J=8.5 Hz)

MS (FAB): Anal. Calc'd. for $C_{24}H_{27}N_3O_4$: 421.20
Found: 422 (MH$^+$)

Example 25

In this Example, 2-ethoxy-1-[(4'-carboxyphenyl)methyl]-1H-benzimidazole-6-carboxylic acid piperidinamide [Compound No. 5; the compound of the formula (6d)] was prepared.

In methanol (8.82 ml), 2-ethoxy-1-[(4'-methoxycarbonylphenyl)methyl]-1H-benzimidazole-6-carboxylic acid piperidinamide (882 mg) prepared in Example 24 was dissolved. Further, a 1N NaOH aqueous solution (8.82 ml) was added to the solution, and the mixture was stirred at room temperature for 1 hour. The reaction solution was acidified with a 1N HCl aqueous solution, and then the whole was extracted with chloroform. An organic layer was dried over anhydrous sodium sulfate and concentrated under vacuum to obtain 2-ethoxy-1-[(4'-carboxyphenyl)methyl]-1H-benzimidazole-6-carboxylic acid piperidinamide (746 mg; yield=87.5%) as a light brown solid.

$^1$H-NMR (60 MHz, CDCl$_3$) δ: 1.10–1.92 (6H, m), 1.43 (3H, t, J=6.5 Hz), 3.23–3.86 (4H, m), 4.69 (2H, q, J=6.5 Hz), 5.26 (2H, s), 7.07–7.50 (4H, m), 7.63 (1H, d, J=8.0 Hz), 7.97 (2H, d, J=8.5 Hz), 9.00 (1H, br. s)

MS (FAB): Anal. Calc'd. for $C_{23}H_{25}N_3O_4$: 407.18
Found: 408 (MH$^+$)

Example 26

In this Example, 2-ethoxy-1-[[4'-(2"-N,N-dimethylaminoethoxycarbonyl)phenyl]methyl]-1H-benzimidazole-6-carboxylic acid piperidinamide [Compound No. 55] was prepared.

In DMF (6.54 ml), 2-ethoxy-1-[(4'-carboxyphenyl)methyl]-1H-benzimidazole-6-carboxylic acid piperidinamide (327 mg) prepared in Example 25 was dissolved. Further, WSCI.HCl (230.8mg), DMAP (49 mg), and dimethylaminoethanol (0.267 ml) were successively added, and the mixture was stirred at room temperature for 17 hours. Distilled water was added to the reaction solution, and then the whole was extracted with chloroform. The resulting crude product was purified by silica gel chromatography (chloroform:methanol=20:1) to obtain 2-ethoxy-1-[[4'-(2"-N,N-dimethylamino-ethoxycarbonyl)-phenyl]methyl]-1H-benzimidazole-6-carboxylic acid piperidinamide (245.8 mg; yield 64.0%) as a light brown solid.

$^1$H-NMR (60 MHz, CDCl$_3$) δ: 1.26–1.79 (6H, m), 1.50 (3H, t, J=7.0 Hz), 2.33 (6H, s), 2.69 (2H, t, J=6.5 Hz), 3.26–3.73 (4H, m), 4.30 (2H, t, J=6.5 Hz), 4.69 (2H, q, J=7.0 Hz), 5.26 (2H, s), 7.09–7.46 (4H, m), 7.59 (1H, d, J=8.0 Hz), 8.03 (2H, d, J=8.5 Hz)

MS (FAB): Anal. Calc'd. for $C_{27}H_{34}N_4O_4$: 478.26
Found: 479 (MH$^+$)

Example 27

In this Example, 2-ethoxy-1-[[4'-(2"-(diethylamino)-ethoxycarbonyl)phenyl]methyl]-1H-benzimidazole-6-carboxylic acid piperidinamide [Compound No. 56] was prepared.

In DMF (25 ml), 2-ethoxy-1-[(4'-carboxyphenyl)methyl]-1H-benzimidazole-6-carboxylic acid piperidinamide (2.5112 g) prepared in Example 25 was dissolved. Further, WSCI.HCl (1.7729 g), DMAP (0.3766 g), and 2-diethylaminoethanol (2.1676 g) were successively added, and the mixture was stirred at room temperature for 17 hours. The reaction solution was poured into distilled water, and then the whole was extracted with chloroform. The resulting crude product was purified by silica gel chromatography (chloroform:methanol=30:1) to obtain 2-ethoxy-1-[[4'-(2'-(diethylamino)ethoxycarbonyl)-phenyl]methyl]-1H-benzimidazole-6-carboxylic acid piperidinamide (2.4954 g; yield=79.9%) as a light yellow oil.

$^1$H-NMR (500 MHz, CDCl$_3$) δ: 1.06 (6H, t, J=7.1 Hz), 1.3–3.9 (10H, b), 1.48 (3H, t, J=7.1 Hz), 2.62 (4H, dd, J=7.1, 14.3 Hz), 2.83 (2H, t, J=6.4 Hz), 4.38 (2H, t, J=6.4 Hz), 4.65 (2H, q, J=7.1 Hz), 5.22 (2H, s), 7.21 (1H, dd, J=1.5, 8.1 Hz), 7.26 (2H, d, J=8.4 Hz), 7.28 (1H, s), 7.53 (1H, d, J=8.1 Hz), 7.99 (2H, d, J=8.4 Hz)

MS (FAB): Anal. Calc'd. for $C_{29}H_{38}N_4O_4$: 506.64

Found: 508 (MH$^+$)

Example 28

In this Example, 2-ethoxy-1-[[4'-(2"-morpholinoethoxycarbonyl)phenyl]methyl]-1H-benzimidazole-6-carboxylic acid piperidinamide [Compound No. 57] was prepared.

In DMF (624 ml), 2-ethoxy-1-[(4'-carboxyphenyl) methyll-1H-benzimidazole-6-carboxylic acid piperidinamide (31.2 g) prepared in Example 25 was dissolved. Further, WSCI.HCl (22.0 g), DMAP (4.68 g), and morpholine ethanol (27.9 ml) were successively added, and the mixture was stirred at room temperature for 24 hours. Distilled water was added to the reaction solution, and then the whole was extracted with chloroform. The resulting crude product was purified by silica gel chromatography (chloroform:methanol=30:1) to obtain 2-ethoxy-1-[[4'-(2"-morpholinoethoxycarbonyl)phenyl]methyl]-1H-benzimidazole-6-carboxylic acid piperidinamide (33.2 g; yield=83.2%) as a light brown solid.

$^1$H-NMR (500 MHz, CDCl$_3$) δ: 1.48 (3H, t, J=7.1 Hz), 1.31–1.9 (6H,m), 2.50–2.60 (4H, m), 2.76 (2H, t, J=5.7 Hz), 3.71–3.34 (8H, m), 4.44 (2H, t, J=5.7 Hz), 4.65 (2H, q, J=7.1 Hz), 5.22 (2H, s), 7.17 (1H, d, J=1.5 Hz), 7.21 (1H, dd, J=8.1, 1.5 Hz), 7.27 (2H, d, J=8.5 Hz), 7.52 (1H, d, J=8.1 Hz), 7.92 (2H, d, J=8.5 Hz)

MS (FAB): Anal. Calc'd. for $C_{29}H_{36}N_4O_5$: 520.27

Found: 521 (MH$^+$)

Examples 29 to 31

In the following Examples 29 to 31, benzimidazole derivatives of the general formula (I) according to the present invention [Compound No. 62; the compound of the formula (5e), Compound No. 58; the compound of the formula (6e), and Compound No. 59; the compound of the general formula (7e)] were prepared from 3-amino-4-nitrobenzoic acid [the compound of the formula (1a)] in accordance with the following scheme [1e] which is similar to the method shown in the scheme [1a].

Scheme [1e]

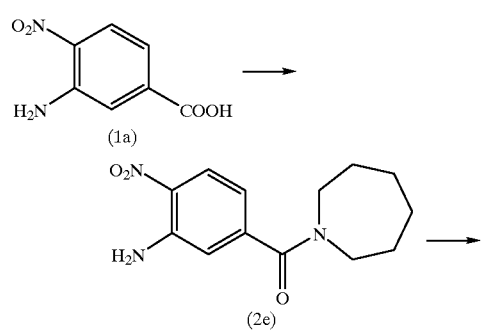

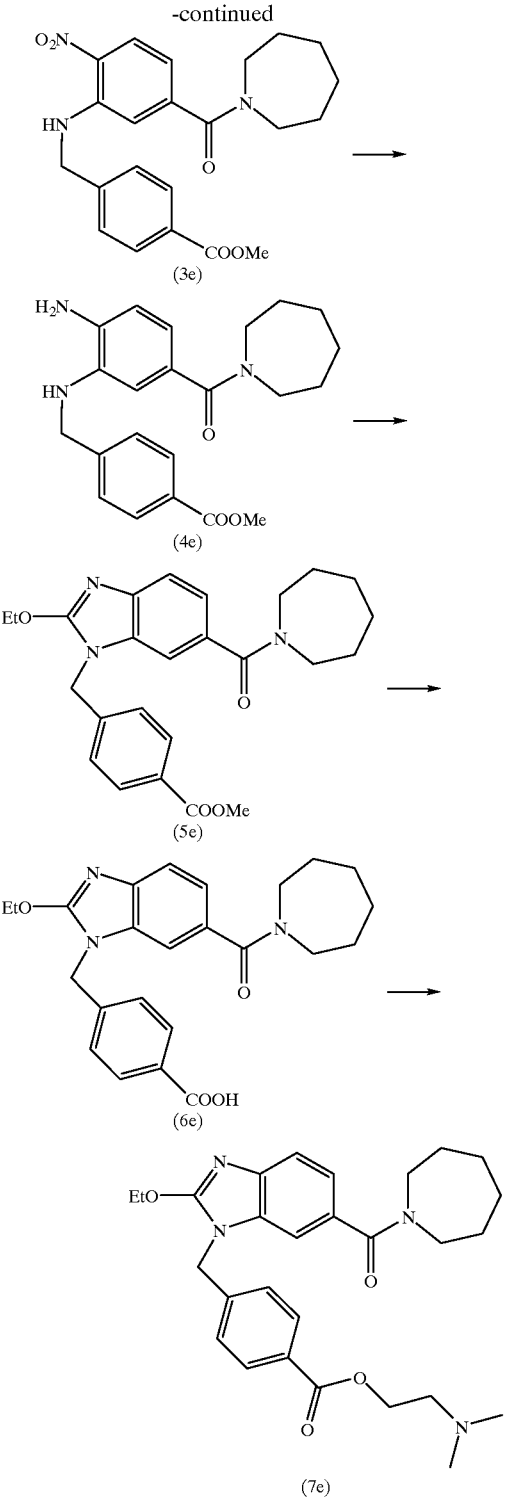

Example 29

In this Example, 2-ethoxy-1-[(4'-methoxycarbonylphenyl)methyl]-1H-benzimidazole-6-carboxylic acidperhydroazepinamide [Compound No. 62; the compound of the formula (5e)] was prepared.

To 4-amino-3-[(4'-methoxycarbonylphenyl) methylamino]benzoic acid perhydroazepinamide [the compound of the formula (4e)] (3.05 g) obtained from 3-amino- 4-nitrobenzoic acid by the method similar to that shown in the scheme [1a], tetraethoxymethane (2.58 ml) and acetic acid (458 μl) were successively added, and the mixture was stirred at 90° C. for 30 minutes. Distilled water was added to the reaction solution, and then the whole was extracted with chloroform. An organic layer was dried over anhydrous sodium sulfate and concentrated under vacuum. The resulting crude product was purified by silica gel chromatography (chloroform:acetone=7:1) to obtain 2-ethoxy-1-[(4'-methoxycarbonylphenyl)methyl]-1H-benzimidazole-6-carboxylic acid perhydroazepinamide (2.50 g; yield=71.8%) as a brown solid.

$^1$H-NMR (500 MHz, CDCl$_3$) δ: 1.07–2.00 (1OH, m), 1.33 (3H, t, J=7.0 Hz), 3.00–3.73 (4H, m), 3.83 (3H, s), 4.60 (2H, q, J=7.OH), 5.17 (2H, s), 6.89–7.33 (4H, m), 7.43 (1H, d, J=8.0 Hz), 7.97 (2H, d, J=8.5 Hz)

MS (FAB): Anal. Calc'd. for C$_{25}$H$_{29}$N$_3$O$_4$: 435.22

Found: 436 (MH$^+$)

Example 30

In this Example, 2-ethoxy-1-[(4'-carboxyphenyl)methyl]-1H-benzimidazole-6-carboxylic acid perhydroazepinamide [CompoundNo. 58; the compound of the formula (6e)] was prepared.

In methanol (25.0 ml), 2-ethoxy-1-[(4'-methoxycarbonylphenyl)methyl]-1H-benzimidazole-6-carboxylic acid perhydroazepinamide (2.50 g) prepared in Example 29 was dissolved. Further, a 1N NaOH aqueous solution (25.0 ml) was added to the solution, and the mixture was stirred at room temperature for 1 hour. The reaction solution was acidified with a 1N HCl aqueous solution, and then the whole was extracted with chloroform. An organic layer was dried over anhydrous sodium sulfate and concentrated under vacuum. The resulting crude product was purified by silica gel chromatography (chloroform:methanol=15:1) to obtain 2-ethoxy-1-[(4 1-carboxyphenyl)methyl]-1H-benzimidazole-6-carboxylic acid perhydroazepinamide (2.14 g; yield=88.4%) as a light brown solid.

$^1$H-NMR (60 MHz, CDCl$_3$) δ: 1.46 (3H, t, J=7 Hz), 1.30–2.00 (8H, m), 3.20–3.80 (4H, m), 4.66 (2H, q, J=7 Hz), 5.16 (2H, s), 7.15 (1H, d, J=7.5 Hz), 7.15 (2H, d, J=8 Hz), 7.20 (1H, s), 7.50 (1H, d, J=7.5 Hz), 7.85 (2H, d, J=8 Hz)

MS (FAB): Anal. Calc'd. for C$_{24}$H$_{27}$N$_3$O$_4$: 421.20

Found: 422 (MH$^+$)

Example 31

In this Example, 2-ethoxy-1-[[4'-(2"-N,N-dimethylaminoethoxycarbonyl)phenyl]methyl]-1H-benzimidazole-6-carboxylic acid perhydroazepinamide [Compound No. 59; the compound of the formula (7e)] was prepared.

In DMF (7.898 ml), 2-ethoxy-1-[(4'-carboxyphenyl)methyl]-1H-benzimidazole-6-carboxylic acid perhydroazepinamide (394.9 mg) prepared in Example 30 was dissolved. Further, WSCI.HCl (269.4 mg), DMAP (57.2 mg), and dimethylaminoethanol (0.282 ml) were successively added, and the mixture was stirred at room temperature for 15.5 hours. Distilled water was added to the reaction solution, and then the whole was extracted with chloroform. The resulting crude product was purified by silica gel chromatography (chloroform:methanol=25:1) to obtain 2-ethoxy-1-[[4'-(2"-N,N-dimethylamino-ethoxycarbonyl)-phenyl]methyl]-1H-benzimidazole-6-carboxylic acid perhydroazepinamide (260.8 mg; yield 56.5%) as a light brown solid.

$^1$H-NMR (60 MHz, CDCl$_3$) δ: 1.03–1.92 (8H, m), 1.50 (3H, t,J=6.5 Hz), 2.30 (6H, s), 2.66 (2H, t, J=7.0 Hz), 3.13–3.73 (4H, m), 4.36 (2H, t, J=7.0 Hz), 4.59 (2H, q, J=6.5 Hz), 5.13 (2H, s), 6.86–7.26 (4H, m), 7.43 (1H, d, J=8.0 Hz), 7.86 (2H, d, J=8.5 Hz)

MS (FAB): Anal. Calc'd. for C$_{28}$H$_{36}$N$_4$O$_4$: 492.27

Found: 493 (MH$^+$)

Examples 32 to 33

In the following Examples 32 to 33, benzimidazole derivatives of the general formula (I) according to the present invention [Compound No. 63; the compound of the formula (5f), and Compound No. 60; the compound of the general formula (6f)] were prepared from 3-amino-4-nitrobenzoic acid [the compound of the formula (1a)] in accordance with the following scheme [1f], which is similar to the method shown in the scheme [1a].

Scheme [1f]

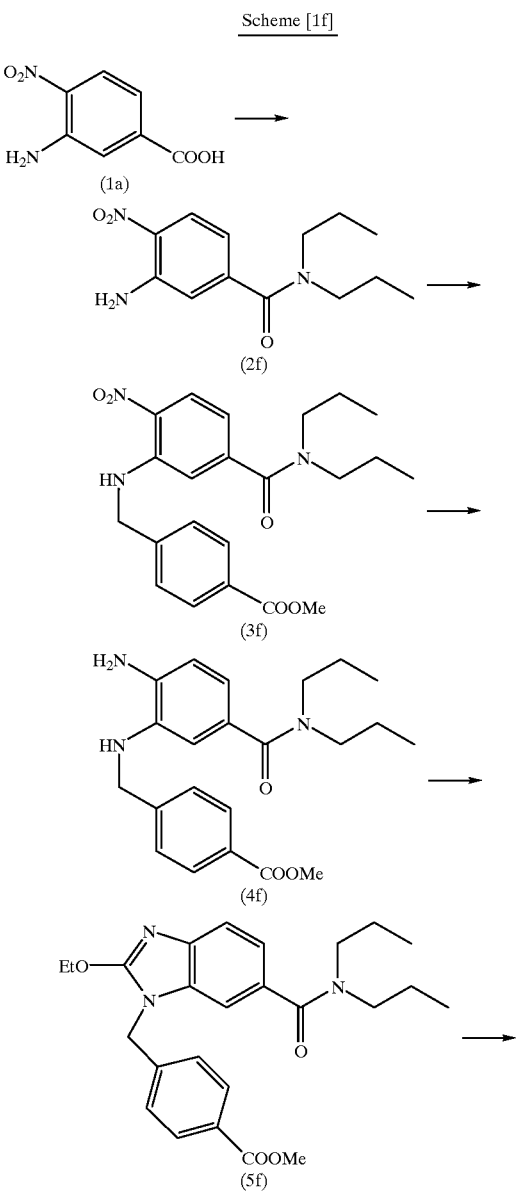

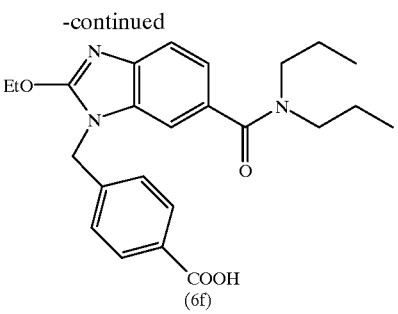

(6f)

Example 32

In this Example, 2-ethoxy-1-[(4'-methoxycarbonylphenyl)-methyl]-1H-benzimidazole-6-carboxylic acid-di-n-propylamide [Compound No. 63; the compound of the formula (5f)] was prepared.

To 4-amino-3-[(4'-methoxycarbonylphenyl)methylamino]-benzoic acid-di-n-propylamide [the compound of the formula (4f)] (6.91 g) obtained from 3-amino-4-nitrobenzoic acid in accordance with the method similar to the scheme (1a], tetraethoxymethane (5.81 ml) and acetic acid (1.03 ml) were successively added, and the mixture was stirred at 90° C. for 40 minutes. Distilled water was added to the reaction solution, and then the whole was extracted with chloroform. An organic layer was dried over anhydrous sodium sulfate and concentrated under vacuum. The resulting crude product was purified by silica gel chromatography (chloroform:acetone=8:1) to obtain 2-ethoxy-1-((4'-methoxycarbonylphenyl)methyl]-1H-benzimidazole-6-carboxylic acid-di-n-propylamide (5.67 g; yield=72.0%) as a brown solid.

$^1$H-NMR (60 MHz, CDCl$_3$) δ: 0.40–2.03 (13H, m), 3.00–3.86 (4H, m), 3.89 (3H, s), 4.63 (2H, q, J=7.0 Hz), 5.20 (2H, s), 6.97–7.63 (5H, m), 7.89 (1H, d, J=8.5 Hz)

MS (FAB): Anal. Calc'd. for $C_{25}H_{31}N_3O_4$: 437.23
Found: 438 (MH$^+$)

Example 33

In this Example, 2-ethoxy-1-[(4'-carboxyphenyl)methyl]-1H-benzimidazole-6-carboxylic acid-di-n-propylamide [Compound No. 60; the compound of the formula (6f)] was prepared.

In methanol (56.7 ml), 2-ethoxy-1-[(4'-methoxycarbonylphenyl)methyl]-1H-benzimidazole-6-carboxylic acid-di-n-propylamide (5.67 g) prepared in Example 32 was dissolved. Further, a 1N NaOH aqueous solution (56.7 ml) was added to the solution, and the mixture was stirred at room temperature for1 hour. The reaction solution was acidified with a 1N HCl aqueous solution, and then the whole was extracted with chloroform. An organic layer was dried over anhydrous sodium sulfate and concentrated under vacuum. The resulting crude product was purified by silica gel chromatography (chloroform:methanol=12:1) to obtain 2-ethoxy-1-[(4'-carboxyphenyl)-methyl]-1H-benzimidazole-6-carboxylic acid-di-n-propylamide (3.44 g; yield=62.6%) as a brown solid.

$^1$H-NMR (60 MHz, CDCl$_3$) δ: 0.86–1.13 (13H, m), 1.43 (3H, t, J=6.5 Hz), 1.16–2.00 (4H, m), 3.00–3.59 (4H, m), 4.59 (2H, q, J=6.5 Hz), 5.17 (2H, s), 6.92–7.30 (4H, m), 7.46 (1H, d, J=8.0 Hz), 7.83 (2H, d, J=8.5 Hz), 8.97 (1H, br. s)

MS (FAB): Anal. Calc'd. for $C_{24}H_{29}N_3$4: 423.22

Found: 424 (MH$^+$)

Examples 34 to 35

In the following Examples 34 to 35, benzimidazole derivatives of the general formula (I) according to-the present invention [Compound No. 64; the compound of the formula (5 g), and compound No. 3; the compound of the formula (6 g)] were prepared from 4-amino-3-[(4'-methoxycarbonylphenyl)methylamino] benzoic acid morpholide [the compound of the formula (4a)] in accordance with the following scheme [1g],which is similar to the method shown in the scheme [1a].

Synthetic pathway [1g]

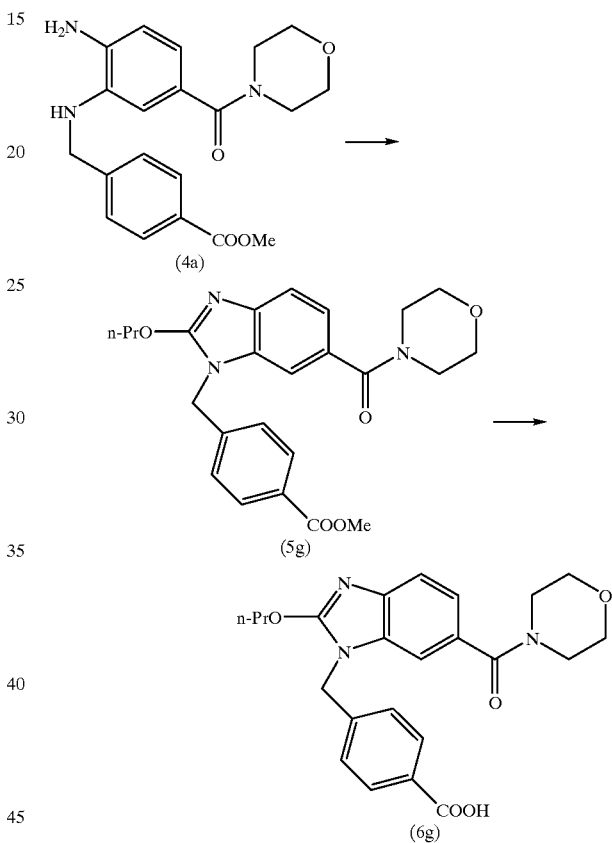

Example 34

In this Example, 2-propoxy-1-[(4'-methoxycarbonylphenyl)methyl]-1H-benzimidazole-6-carboxylic acid morpholide [Compound No. 64; the compound of the formula (5 g)] was prepared.

To 4-amino-3-[(4 '-methoxycarbonylphenyl) methylamino]-benzoic acid morpholide [the compound of the formula (4a)] (3.68 g) prepared in Example 3, tetra-n-propoxymethane (4.23 ml) and acetic acid (0.570 ml) were successively added, and the mixture was stirred at 90° C. for 30 minutes. Distilled water was added to the reaction solution, and then the whole was extracted with chloroform. An organic layer was dried over anhydrous sodium sulfate and concentrated under vacuum. The resulting crude product was purified by silica gel chromatography (chloroform:acetone=5:1) to obtain 2-propoxy-1-[(4'-methoxycarbonylphenyl)methyl]-1H-benzimidazole-6-carboxylic acid morpholide (2.33 g; yield=53.4%) as a brown solid.

$^1$H-NMR (60 MHz, CDCl$_3$) δ: 1.03 (3H, t, J=6.5 Hz), 1.69–2.07 (2H, m), 3.50–3.86 (8H, m), 4.66 (2H, t, J=6.5 Hz), 5.33 (2H, s), 7.17–7.79 (5H, m), 8.13 (1H, d, J=8.5 Hz)

MS (FAB): Anal. Calc'd. for C$_{24}$H$_{27}$N$_3$O$_5$: 437.49

Found: 438 (MH$^+$)

Example 35

In this Example, 2-n-propoxy-1-[(4'-carboxyphenyl)methyl]-1H-benzimidazole-6-carboxylic acid morpholide [Compound No. 3; the compound of the formula (6 g)] was prepared.

In methanol (23.3 ml), 2-n-propoxy-1-[(4'-methoxycarbonylphenyl)methyl]-1H-benzimidazole-6-carboxylic acid morpholide (2.33 g) prepared in Example 34 was dissolved. Further, a 1N NaOH aqueous solution (23.3 ml) was added to the solution, and the mixture was stirred at room temperature for 1 hour. The reaction solution was acidified with a 1N HCl aqueous solution, and then the whole was extracted with chloroform. An organic layer was dried over anhydrous sodium sulfate and concentrated under vacuum. The resulting crude product was purified by silica gel chromatography (chloroform:methanol=10:1) to obtain 2-n-propoxy-1-[(4'-carboxyphenyl)methyl]-1H-benzimidazole-6-carboxylic acid morpholide (1.80 g; yield=79.6%) as a brown solid.

$^1$H-NMR (60 MHz, CDCl$_3$) δ: 1.00 (3H, t, J=6.5 Hz), 1.53–2.13 (2H, m), 3.36–3.97 (8H, m), 4.59 (2H, t, J=6.5 Hz), 5.26 (2H, s), 6.66–7.46 (4H, m), 7.59 (1H, d, J=8.0 Hz), 7.94 (2H, d, J=8.5 Hz)

MS (FAB): Anal. Calc'd. for C$_{23}$H$_{25}$N$_3$O$_5$: 423.18

Found: 424 (MH$^+$)

Example 36

Acute toxicity was evaluated in this Example. As a compound to be examined, 2-ethoxy-1-[[4'-(2"-N,N-dimethylamino-ethoxycarbonyl)phenyl]methyl]-1H-benzimidazole-6-carboxylic acid morpholide (Compound No. 13) prepared in Example 6 was used.

Five-week-old ICR female mice (5 mice per group) were bredfor acclimation for a week. Then, Compound No. 13 was dissolved or suspended in 0.5% methylcellulose aqueous solution, and orally administered to the mice in a single dosage (500 mg/kg). The number of deaths was observed for 6 days after the administration. Further, as to Compound No. 55, Compound No. 57, Compound No. 59, and Compound No. 65 prepared in Examples 26, 28, 31, and 23, respectively, acute toxicity was also evaluated. The results are shown in Table 4.

TABLE 4

| Compound No. | Number of deaths/number of survivals |
|---|---|
| 13 | 0/5 |
| 55 | 0/5 |
| 57 | 0/5 |
| 59 | 0/5 |
| 65 | 0/5 |

Example 37

In this Example, a binding assay was carried out. That is, the affinity to the angiotensin II receptor subtype 1 orsubtype 2 was evaluated in accordance with the method described in Biochem. Pharmacol., 33, 4057–4062 (1984).

Specifically, the measurement of the total binding in the presence of each drug was performed as follows:

A mixture (final volume=0.25 ml) of a drug in a given concentration (the drug was dissolved in DMSO, and diluted to a double volume with a buffer attached to a drug discovery system to prepare a sample for the assay; 0.025 ml), a tracer (0.025 ml), and receptors (0.2 ml) was incubated [in the case of the angiotensin II receptor subtype 1 (AT$_1$), at room temperature for 3 hours, and in the case of the subtype 2 (AT$_2$), at 37° C. for 1 hour]. Then, the reaction mixture was filtered with suction (a GF/C filter was used in AT$_1$, and a GF/B filter was used in AT$_2$). The filter papers after filtration with suction (the tracer bound to the receptors) were counted by a γ-well counter (ARC-500, Aloka). The non-specific bindings were measured by repeating the above method, except that a large excess amount of a displacer was added. The specific binding of the drug in the given concentration was calculated by subtracting the non-specific binding from the total binding, respectively.

In AT$_1$ and AT$_2$, the percentages found to inhibit the bindings of radioactive ligands (tracer) to receptors by the drugs to be tested (IC$_{50}$ value of concentration to show 50% inhibition, or binding inhibition % in 10 μM) were measured, using the drugs to be tested and control drugs in the given concentration. The results are shown in Table 5.

TABLE 5

| Compound No. | IC$_{50}$ AT$_1$ (nM) | Binding inhibition % in 100 μM AT$_1$ | AT$_2$ |
|---|---|---|---|
| 1 |  | 45 | 0 |
| 2 |  | 0 | 0 |
| 3 |  | 45 | 0 |
| 4 |  | 45 | 0 |
| 5 |  | 50 | 0 |
| 6 |  | 50 | 0 |
| 7 |  | 50 | 0 |
| 8 |  | 50 | 0 |
| 9 |  | 10 | 0 |
| 10 |  | 40 | 0 |
| 11 |  | 10 | 0 |
| 12 |  | 40 | 0 |
| 20 |  | 45 | 0 |
| 22 |  | 45 | 0 |
| 23 |  | 45 | 0 |
| 58 |  | 50 | 0 |
| DuP753 | 20 |  | 0 |

In AT$_1$,

| | |
|---|---|
| receptor: | from adrenal glands in rabbits |
| tracer: | $^3$H-angiotensin II |
| control drug: | DuP753 |
| (displacer): | DuP753 |

In AT$_2$,

| | |
|---|---|
| receptor: | from cerebellar cortex in bovine |
| tracer: | $^{125}$I-Tyr$^4$-angiotensin II |
| control drug: | angiotensin II (human) |
| (displacer): | angiotensin II (human) |

As apparent from Table 5, the binding inhibition to the angiotensin II receptor subtype 1 was 50% or less at 10 μM. The IC$_{50}$ value of DuP753 used as a reference substance was 20 nM, whereas the benzimidazole derivatives of the general formula (I) according to the present invention exhibit no inhibitory effect on the subtype 1 receptor. That the benzimidazole derivatives of the general formula (I) according to the present invention exhibit no binding activity to the subtype 1 receptor shows that such compounds have a completely different action mechanism from conventional ACE inhibitors or angiotensin II antagonists.

Example 38

In this Example, an action to lower blood pressure was evaluated. That is, each of 2-ethoxy-1-[[4'- (2'-N,N-dimethylamino-ethoxycarbonyl) phenyl]methyl]-1H-benzimidazole-6-carboxylic acid morpholide (Compound No. 13) prepared in Example 6, 2-ethoxy-1-[[4'-(2"-morpholinoethoxycarbonyl)-phenyl]methyl]-1H-benzimidazole-6-carboxylic acid piperidinamide (Compound No. 57) prepared in Example 28, or the reference substance was forcibly orally administered to kidney disease model rats, and the action of lowering the blood pressure was observed. The kidney disease model rats were prepared by a ligature of branches of renal artery in accordance with a conventional method. Namely, the left hilum renalis of Sprague-Dawley female rats was exposed under anesthesia, and one of four secondary branches of the renal artery was left unligated, while the remaining three branches were ligated, respectively. After a week, the hilum renalis (artery, vein, and ureter) of the right kidney were further ligated to thereby prepare rats whose renal function was lowered to approximately ⅛ of the normal function. Each group consisted of eight rats. The drugs to be tested (20 mg/kg) were administered to each administering group, and only water was administered to a control group. Two days after the administration, the systolic blood pressure was measured by the tail cuff method using a blood pressure measuring apparatus (UR$^{5000}$; Ueda). The average of the blood pressures is shown in Table 6.

TABLE 6

| Compound No. | Blood pressure (mmHg) |
|---|---|
| 13 | 208 |
| 57 | 205 |
| control | 210 |
| DuP753 | 130 |

In comparison with the control group, the reference substance (DuP753) clearly exhibited the action of lowering the blood pressure. On the contrary, an influence on the blood pressure was not substantially observed in each of the groups wherein Compound No. 13 or Compound No. 57 was administered.

Example 39

In this Example, an action to kidney diseases was evaluated on the basis of a renal function indicatory value. As compounds to be examined, 2-ethoxy-1-[[4'-(2"-N,N-dimethylamino-ethoxycarbonyl)phenyl]methyl]-1H-benzimidazole- 6-carboxylic acid morpholide (Compound No. 13) prepared in Example 6, and 2-ethoxy-1-[[4'-(2"-morpholinoethoxycarbonyl)phenyl]methyl]-1H-benzimidazole-6-carboxylic acid piperidinamide (Compound No. 57) prepared in Example 28 were used.

The kidney disease model rats were prepared as in Example 38. Fifteen groups (8 rats per group) were prepared in a manner such that there was no major difference between the groups in the serum creatinine value and the blood urea nitrogen value indicating renal function. The rats in each group were allowed to freely take up food and water. To the rats in the administering group, Compound No. 13, Compound No. 57, or the reference substance (DuP753) were administered at the dose of 20 mg/kg/day every day. To the rats in the control group, only water was forcibly orally administered every day. After two weeks, 0.2 ml of blood was collected from the carotid artery of the rats under anesthesia, and centrifuged to obtain serum. Using 25 µl of the serum, the serum creatinine (Scr) was measured by a creatinine analytical instrument (Beckman). Using 10 µl of the serum, the blood urea nitrogen (BUN) was measured by a BUN analytical instrument (Beckman). The creatinine clearance was evaluated as follows:

After the serum creatinine measurement, rats were placed in urinary metabolic cages for 24 hours to collect urine. A urinary creatine concentration (Ucr) was measured by a creatinine analytical instrument, and a total volume of urination (Uvol) was also measured. The creatinine clearance (CCr) was calculated by the following formula:

$$CCr\,(\text{ml}/\min) = \frac{Ucr \times Uvol}{Scr \times 24 \times 60\,(\min)}$$

In the above formula, the unit of "Ucr" and "Scr" is "mg/ml" and the unit of "Uvol" is "ml".

The results are shown in Table 7.

TABLE 7

| Compound No. | Creatinine mg/dl | Blood urea nitrogen mg/dl | Creatinine clearance ml/min |
|---|---|---|---|
| 13 | 1.5 | 75 | 0.35 |
| 57 | 1.5 | 72 | 0.33 |
| control | 2.0 | 100 | 0.22 |
| DuP753 | 1.6 | 80 | 0.32 |

When Compound No. 13 or Compound No. 57 were administered, the serum creatinine value and the blood urea nitrogen value, which increase with an aggravation of renal failure, clearly became lower values, and the creatinine clearance indicating renal function was clearly improved in comparison with the control substance. The effects were comparable to those of the reference substance, and it was shown that Compound No. 13 and Compound No. 57 do not substantially exhibit a conventional angiotensin II receptor antagonism and blood pressure lowering action, but alleviate kidney diseases.

Example 40

In this Example, an action to survival time of kidney diseased animals was evaluated. As compounds to be examined, 2-ethoxy-1-[[4'-(2"-N,N-dimethylamino-ethoxycarbonyl)-phenyl]methyl]-1H-benzimidazole-6-carboxylic acid morpholide (Compound No. 13) prepared in Example 6, and 2-ethoxy-1-[[4'-(2"-morpholinoethoxycarbonyl)phenyl]methyl]-1H-benzimidazole-6-carboxylic acid piperidinamide (Compound No. 57) prepared in Example 28 were used.

The kidney disease model rats were prepared as in Example 38. Fifteen groups (8 rats per group) were prepared in a manner such that there was no major difference between the groups in the serum creatinine value and the blood urea nitrogen value indicating renal function. The rats in each group were allowed to freely take up food and water. To the rats in the administering group, Compound No. 13, Compound No. 57, or the reference substance (DuP753) were administered at the dose of 20 mg/kg/day every day. To the rats in the control group, only water was forcibly orally administered every day. If kidney diseases are aggravated, the rat will die of uremia. Thus, the survival time was observed as a comprehensive indication of the improvement of the effect on the kidney diseases. The results are shown in Table 8. The observation period was eight weeks. Thus if all rats survived, the average survival time is eight weeks, and is an upper limit.

TABLE 8

| Compound No. | Average survival time (weeks) |
| --- | --- |
| 13 | 7.5 |
| 57 | 7.5 |
| control | 5.0 |
| DuP753 | 6.9 |

Compound No. 13 or Compound No. 57 clearly prolonged the survival time of the kidney disease model rats. The effect was comparable or superior to that of the reference substance. It was shown that Compound No. 13 and Compound No. 57 do not substantially exhibit known angiotensin II receptor antagonism and blood pressure lowering action, but prolonged the survival time of the rats having kidney diseases.

Example 41

In this Example, an action on a weight of a heart was evaluated. More particularly, 21-week-old SHR rats were divided into a control group (8 rats) and a test group (7 rats). The rats in the test group were allowed to freely drink a solution prepared by dissolving 2-ethoxy-1-[[4'-(2"-N,N-dimethylamino-ethoxycarbonyl)phenyl]methyl]-1H-benzimidazole-6-carboxylic acid morpholide (Compound No. 13) prepared in Example 6 or 2-ethoxy-1-[[4'-(2'-morpholinoethoxycarbonyl)-phenyl]methyl]-1H-benzimidazole-6-carboxylic acid piperidinamide (Compound No. 57) prepared in Example 28 for 20 weeks (20 mg/kg). After the oral administration was finished, the heart was taken, and the weight of the heart was measured. Body weights, blood pressures, heart weights, and relative weight ratios (average±standard deviation) are listed in Table 9.

TABLE 9

| Group | Body weight (g) | Blood pressure (mmHg) | Heart weight (g) | Relative weight ratio (%) |
| --- | --- | --- | --- | --- |
| Control group | 423 ± 17 | 224 ± 49 | 1.430 ± 0.082 | 0.338 ± 0.012 |
| Test group (Compound No. 13) | 424 ± 11 | 232 ± 12 | 1.392 ± 0.034 | 0.328 ± 0.007 |
| Test group (Compound No. 57) | 429 ± 17 | 207 ± 14 | 1.390 ± 0.077 | 0.324 ± 0.012 |

The test results show that the heart weight based on hypercardia was significantly reduced, and thus, Compound No. 13 or 57 suppresses myocardiopathy without inducing a lowering of blood pressure.

Example 42

In this Example, tablets (230 mg/tablet) were prepared by mixing 2-ethoxy-1-[[4'-(2"-N,N-dimethylamino-ethoxycarbonyl)-phenyl]methyl]-1H-benzimidazole-6-carboxylic acid morpholide (Compound No. 13) (10 mg) prepared in Example 6, lactose (36 mg), cornstarch (150 mg), crystalline cellulose (29 mg), and magnesium stearate (5 mg), and pressing.

Industrial Applicability

The benzimidazole derivative of the formula (I) or the pharmaceutically acceptable salt thereof according to the present invention provides a sufficient effect on kidney diseases and heart diseases without affecting the blood pressure. Therefore, it is possible to effectively and appropriately treat kidney diseases or heart diseases with the compounds of the present invention, while controlling the blood pressure at a desired level by the use of a suitable antihypertensive agent if necessary.

As above, the present invention was explained with reference to particular embodiments, but modifications and improvements obvious to those skilled in the art are included in the scope of the present invention.

What is claimed is:

1. A benzimidazole derivative of the general formula (I):

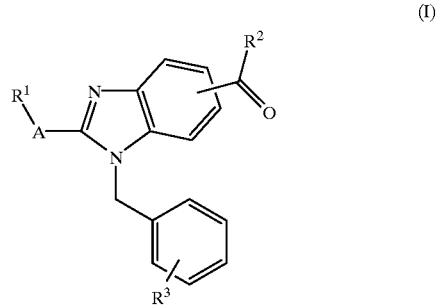

(I)

wherein A is —O— or —NH—;

$R^1$ is an aliphatic hydrocarbon group having 1 to 8 carbon atoms, or an aliphatic hydrocarbon group having 1 to 8 carbon atoms which is substituted with one or more halogen atoms;

$R^2$ is —OH, —$OR^{10}$, —$NHR^{11}$, —$NR^{12}R^{13}$, or —$NH_2$, or a three- to seven-membered saturated cycloaliphatic amino group which may be optionally interrupted by one or more nitrogen, oxygen, or sulfur atoms, or a three- to seven-membered saturated cycloaliphatic hydrocarbon group containing at least one nitrogen atom in the ring which is substituted with one or more aliphatic hydrocarbon groups having 1 to 8 carbon atoms, or a three- to seven-membered saturated cycloaliphatic hydrocarbon group containing at least one nitrogen atom in the ring which is substituted with one or more aliphatic hydrocarbon groups having 1 to 8 carbon atoms which is substituted with one or more halogen atoms;

$R^3$ is —COOH, —$COOR^4$, or —OH;

$R^4$ is an aliphatic hydrocarbon group having 1 to 8 carbon atoms, an aliphatic hydrocarbon group having 1 to 8 carbon atoms which is substituted with one or more halogen atoms, —$(CH_2)_mNR^{14}R^{15}$, —$(CH_2)_nR^5$, —$(CH_2)_pCH(NR^{16}R^{17})COOR^{18}$, —$R'$—$COOR^{19}$, —$CH(R^{20})OC(=O)R^7$, or —$CH(R^{21})OC(=O)OR^8$;

$R^5$ is a three- to seven-membered saturated cycloaliphatic amino group which may be optionally interrupted by one or more nitrogen, oxygen, or sulfur atoms, or a three- to seven-membered saturated cycloaliphatic hydrocarbon group containing at least one nitrogen atom in the ring which is substituted with one or more aliphatic hydrocarbon groups having 1 to 8 carbon atoms, or a three- to seven-membered saturated cycloaliphatic hydrocarbon group containing at least one nitrogen atom in the ring which is substituted with one or more aliphatic hydrocarbon groups having 1 to 8 carbon atoms which is substituted with one or more halogen atoms, or a three- to seven-membered unsaturated heterocyclic group;

$R^6$ is a three- to seven-membered saturated cycloaliphatic hydrocarbon group containing at least one nitrogen atom in the ring which may be optionally substituted with one or more aliphatic hydrocarbon groups having 1 to 8 carbon atoms, or a three- to seven-membered saturated cycloaliphatic hydrocarbon group containing at least one nitrogen atom in the ring which may be optionally substituted with one or more aliphatic hydrocarbon groups having 1 to 8 carbon atoms which is substituted with one or more halogen atoms;

$R^7$ and $R^8$ are —$(CH_2)_r R^9$;

$R^9$ is a hydrogen atom, an aliphatic hydrocarbon group having 1 to 8 carbon atoms, an aliphatic hydrocarbon group having 1 to 8 carbon atoms which is substituted with one or more halogen atoms, or —$NR^{22}R^{23}$;

$R^{10}$, $R^{11}$, $R^{12}$, $R^{13}$, $R^{14}$, $R^{15}$, $R^{16}$, $R^{17}$, $R^{18}$, $R^{19}$, $R^{22}$, and $R^{23}$ are independently an aliphatic hydrocarbon group having 1 to 8 carbon atoms, or an aliphatic hydrocarbon group having 1 to 8 carbon atoms which is substituted with one or more halogen atoms;

$R^{20}$ and $R^{21}$ are a hydrogen atom, an aliphatic hydrocarbon group having 1 to 8 carbon atoms, or an aliphatic hydrocarbon group having 1 to 8 carbon atoms which is substituted with one or more halogen atoms; and m, n, p, and r are 0 or an integer of 1 to 6, or a salt thereof.

2. A benzimidazole derivative according to claim 1, wherein A is —O— or —NH—;

$R^1$ is an aliphatic hydrocarbon group having 1 to 5 carbon atoms, or an aliphatic hydrocarbon group having 1 to 5 carbon atoms which is substituted with one or more halogen atoms;

$R^2$ is —OH, —$OR^{10}$, —$NHR^{11}$, —$NR^{12}R^{13}$, or —$NH_2$, or a three- to six-membered saturated cycloaliphatic amino group which may be optionally interrupted by one or more nitrogen, oxygen, or sulfur atoms, or a three- to six-membered saturated cycloaliphatic hydrocarbon group containing at least one nitrogen atom in the ring which is substituted with one or more aliphatic hydrocarbon groups having 1 to 4 carbon atoms, or a three- to six-membered saturated cycloaliphatic hydrocarbon group containing at least one nitrogen atom in the ring which is substituted with one or more aliphatic hydrocarbon groups having 1 to 4 carbon atoms which is substituted with one or more halogen atoms;

$R^3$ is —COOH, —$COOR^4$, or —OH;

$R^4$ is an aliphatic hydrocarbon group having 1 to 5 carbon atoms, an aliphatic hydrocarbon group having 1 to 5 carbon atoms which is substituted with one or more halogen atoms, —$(CH_2)_m NR^{14}R^{15}$, —$(CH_2)_n R^5$, —$(CH_2)_p CH(NR^{16}R^{17})COOR^{18}$, —$R^6$—$COOR^{19}$, —$CH(R^{20})OC(=O) R^7$, or —$CH(R^{21})OC(=O)OR^8$;

$R^5$ is a three- to six-membered saturated cycloaliphatic amino group which may be optionally interrupted by one or more nitrogen, oxygen, or sulfur atoms, or a three- to six-membered saturated cycloaliphatic hydrocarbon group containing at least one nitrogen atom in the ring which is substituted with one or more aliphatic hydrocarbon groups having 1 to 4 carbon atoms, or a three- to six-membered saturated cycloaliphatic hydrocarbon group containing at least one nitrogen atom in the ring which is substituted with one or more aliphatic hydrocarbon groups having 1 to 4 carbon atoms which is substituted with one or more halogen atoms, or a three- to six-membered unsaturated heterocyclic group;

$R^6$ is a three- to six-membered saturated cycloaliphatic hydrocarbon group containing at least one nitrogen atom in the ring which may be optionally substituted with one or more aliphatic hydrocarbon groups having 1 to 4 carbon atoms, or a three- to six-membered saturated cycloaliphatic hydrocarbon group containing at least one nitrogen atom in the ring which may be optionally substituted with one or more aliphatic hydrocarbon groups having 1 to 4 carbon atoms which is substituted with one or more halogen atoms;

$R^7$ and $R^8$ are —$(CH_2)_r R^9$;

$R^9$ is a hydrogen atom, an aliphatic hydrocarbon group having 1 to 5 carbon atoms, an aliphatic hydrocarbon group having 1 to 5 carbon atoms which is substituted with one or more halogen atoms, or —$NR^{22} R^{23}$;

$R^{10}$, $R^{11}$, $R^{12}$, $R^{13}$, $R^{14}$, $R^{15}$, $R^{16}$, $R^{17}$, $R^{18}$, $R^{19}$, $R^{22}$, and $R^{23}$ are independently an aliphatic hydrocarbon group having 1 to 6 carbon atoms, or an aliphatic hydrocarbon group having 1 to 6 carbon atoms which is substituted with one or more halogen atoms;

$R^{20}$ and $R^{21}$ are ahydrogen atom, an liphatic hydrocarbon group having 1 to 6 carbon atoms, or an aliphatic hydrocarbon group having 1 to 6 carbon atoms which is substituted with one or more halogen atoms; and m, n, p, and r are 0 or an integer of 1 to 5, or a salt thereof.

3. A benzimidazole derivative according to claim 2, wherein A is —O— or —NH—;

$R^1$ is an aliphatic hydrocarbon group having 2 to 4 carbon atoms;

$R^2$ is a three- to six-membered saturated cycloaliphatic amino group which may be optionally interrupted by one or more nitrogen, oxygen, or sulfur atoms, or —OH, —$OR^{10}$, —$NHR^{11}$, —$NR^{12}R^{13}$, or —$NH_2$;

$R^3$ is —COOH, —$COOR^4$, or —OH;

$R^4$ is an alkyl group having 1 to 5 carbon atoms, —$(CH_2)_m NR^{14}R^{15}$, —$(CH_2)_n R^5$, or —$CH_2OC(=O) R^7$;

$R^5$ is a three- to seven-membered saturated cycloaliphatic amino group which may be optionally interrupted by one or more nitrogen, oxygen, or sulfur atoms;

$R^7$ is —$(CH_2)_r CH_3$;

$R^{10}$, $R^{11}$, $R^{12}$, $R^{13}$, $R^{14}$, and $R^{15}$ are independently an alkyl group having 1 or 2 carbon atoms;

m is 0 or an integer of 1 or 2;

n is an integer of 1 to 5; and r is 0 or an integer of 1 to 5, or a salt thereof.

4. A benzimidazole derivative according to any one of claims 1 to 3, wherein —C(=O)$R^2$ is at a 5- or 6-position of the benzimidazole ring, and $R^3$ is at a 4-position of the phenyl ring, or a salt thereof.

5. A benzimidazole derivative according to claim 4, wherein —C(=O)$R^2$ is at a 6-position of the benzimidazole ring, or a salt thereof.

6. A benzimidazole derivative according to claim 1, wherein A is —O—;

$R^1$ is an alkyl group having 2 to 4 carbon atoms;

$R^2$ is a 1-pyrrolidinyl or piperidino group;

$R^3$ is —$COOR^4$;

$R^4$ is —$(CH_2)$ nR $R^5$ is a morpholino group;

n is an integer of 1 to 3;

—C(=O)$R^2$ is at a 6-position of the benzimidazole ring; and $R^3$ is at a 4-position of the phenyl ring, or a salt thereof.

7. A pharmaceutical composition characterized by comprising a compound of the general formula (I)

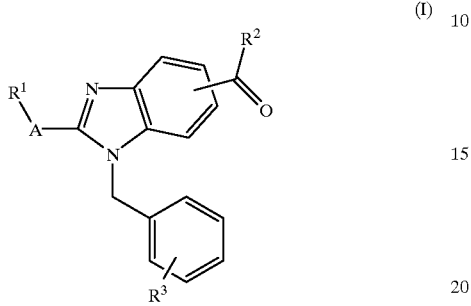

wherein A is —O— or —NH—;

$R^1$ is an aliphatic hydrocarbon group having 1 to 8 carbon atoms, or an aliphatic hydrocarbon group having 1 to 8 carbon atoms which is substituted with one or more halogen atoms;

$R^2$ is —OH, —O$R^{10}$, —NH$R^{11}$, —N$R^{12}R^{13}$, or —NH$_2$, or a three- to seven-membered saturated cycloaliphatic amino group which may be optionally interrupted by one or more nitrogen, oxygen, or sulfur atoms, or a three- to seven-membered saturated cycloaliphatic hydrocarbon group containing at least one nitrogen atom in the ring which is substituted with one or more aliphatic hydrocarbon groups having 1 to 8 carbon atoms, or a three- to seven-membered saturated cycloaliphatic hydrocarbon group containing at least one nitrogen atom in the ring which is substituted with one or more aliphatic hydrocarbon groups having 1 to 8 carbon atoms which is substituted with one or more halogen atoms;

$R^3$ is —COOH, —COO$R^4$, or —OH;

$R^4$ is an aliphatic hydrocarbon group having 1 to 8 carbon atoms, an aliphatic hydrocarbon group having 1 to 8 carbon atoms which is substituted with one or more halogen atoms, —(CH$_2$)$_m$M$^{14}$R$^{15}$, —(CH$_2$)$_n$R$^5$, —(CH$_2$)$_p$CH(NR$^{16}$R$^{17}$)COOR$^{18}$, —R$^6$—COOR$^{19}$, CH(R$^{20}$)OC(=O)R$^7{}_1$ or —CH(R$^{21}$)OC(=O)OR$^8$;

$R^5$ is a three- to seven-membered saturated cycloaliphatic amino group which may be optionally interrupted by one or more nitrogen, oxygen, or sulfur atoms, or a three- to seven-membered saturated cycloaliphatic hydrocarbon group containing at least one nitrogen atom in the ring which is substituted with one or more aliphatic hydrocarbon groups having 1 to 8 carbon atoms, or a three- to seven-membered saturated cycloaliphatic hydrocarbon group containing at least one nitrogen atom in the ring which is substituted with one or more aliphatic hydrocarbon groups having 1 to 8 carbon atoms which is substituted with one or more halogen atoms, or a three- to seven-membered unsaturated heterocyclic group; $R^6$ is a three- to seven-membered saturated cycloaliphatic hydrocarbon group containing at least one nitrogen atom in the ring which may be optionally substituted with one or more aliphatic hydrocarbon groups having 1 to 8 carbon atoms, or a three- to seven-membered saturated cycloaliphatic hydrocarbon group containing at least one nitrogen atom in the ring which may be optionally substituted with one or more aliphatic hydrocarbon groups having 1 to 8 carbon atoms which is substituted with one or more halogen atoms;

$R^7$ and $R^8$ are —(CH$_2$)$_r$R$^9$;

$R^9$ is a hydrogen atom, an aliphatic hydrocarbon group having 1 to 8 carbon atoms, an aliphatic hydrocarbon group having 1 to 8 carbon atoms which is substituted with one or more halogen atoms, or —NR$^{22}$R$^{23}$;

$R^{10}$, $R^{11}$, $R^{12}$, $R^{13}$, $R^{14}$, $R^{15}$, $R^{16}$, $R^{17}$, $R^{18}$, $R^{19}$, $R^{22}$, and $R^{23}$ are independently an aliphatic hydrocarbon group having 1 to 8 carbon atoms, or an aliphatic hydrocarbon group having 1 to 8 carbon atoms which is substituted with one or more halogen atoms;

$R^{20}$ and $R^{21}$ are a hydrogen atom, an aliphatic hydrocarbon group having 1 to 8 carbon atoms, or an aliphatic hydrocarbon group having 1 to 8 carbon atoms which is substituted with one or more halogen atoms; and m, n, p, and r are 0 or an integer of 1 to 6, or a pharmaceutically acceptable salt thereof, and a pharmaceutically acceptable carrier or diluent.

8. An agent for treating or preventing kidney diseases comprising a pharmaceutical composition according to claim 7.

9. An agent for treating or preventing heart diseases comprising a pharmaceutical composition according to claim 7.

10. A method for treating or preventing kidney diseases or heart diseases, comprising administering to an individual in need thereof an effective amount of a compound of the general formula (I) according to claim 1 or a pharmaceutically acceptable salt thereof.

* * * * *

UNITED STATES PATENT AND TRADEMARK OFFICE
CERTIFICATE OF CORRECTION

PATENT NO.   : 6,242,445 B1
DATED        : June 5, 2001
INVENTOR(S)  : Mikiro Yanaka; Shigeru Suzuki; Fuyuhiko Nishijima; Hiroshi Takahashi; Mikio Sugano; Hiroshi Maruoka; Toru Yamazaki; Toshikazu Dewa; Hiroyuki Enari; and Michihito Ise It is certified that error appears in the above-identified patent and that said Letters Patent is hereby corrected as shown below:

Claim 1,
Line 59, should read -- $-(CH_2)_p CH(NR^{16}R^{17})COOR^{18}, -R^6-COOR^{19}$, --

Column 46, claim 2,
Line 27, should read -- $R^{20}$ and $R^{21}$ are a hydrogen atom, an aliphatic hydrocarbon --

Column 46, claim 6,
Line 67, should read -- $R^4$ is $-(CH_2)_n R^5$; --

Column 47, claim 7,
Line 46, should read -- Halogen atoms, $-(CH_2)_m NR^{14}R^{15}$, $-(CH_2)_n R^5$, --
Line 48, should read -- $-CH(R^{20})OC(=O)R^7$, or $-CH(R^{21})OC(=O)R^8$; --

Signed and Sealed this

First Day of January, 2002

Attest:

*Attesting Officer*

JAMES E. ROGAN
*Director of the United States Patent and Trademark Office*